US007105562B2

(12) United States Patent
Zhang et al.

(10) Patent No.: US 7,105,562 B2
(45) Date of Patent: Sep. 12, 2006

(54) GEOMETRICALLY RESTRICTED 3-CYCLOPENTYLIDENE-1,3-DIHYDROINDOL-2-ONES AS POTENT PROTEIN TYROSINE KINASE INHIBITORS

(75) Inventors: Fang-Jie Zhang, Sunnyvale, CA (US); Jingrong Cui, San Diego, CA (US); Chung Chen Wei, Foster City, CA (US); Peng Cho Tang, Moraga, CA (US)

(73) Assignee: Sugen, Inc., San Diego, CA (US)

( * ) Notice: Subject to any disclaimer, the term of this patent is extended or adjusted under 35 U.S.C. 154(b) by 0 days.

(21) Appl. No.: 10/911,637

(22) Filed: Aug. 5, 2004

(65) Prior Publication Data

US 2005/0038066 A1 Feb. 17, 2005

Related U.S. Application Data

(60) Provisional application No. 60/492,782, filed on Aug. 6, 2003.

(51) Int. Cl.
*A61K 31/404* (2006.01)
*C07D 209/52* (2006.01)
*C09B 71/02* (2006.01)
*C09B 71/04* (2006.01)

(52) U.S. Cl. ............... 514/414; 548/457; 548/459
(58) Field of Classification Search .............. None
See application file for complete search history.

(56) References Cited

U.S. PATENT DOCUMENTS

| 4,966,849 | A |   | 10/1990 | Vallee et al. |
| 5,217,999 | A |   | 6/1993  | Levitzki et al. |
| 5,292,737 | A | * | 3/1994  | Defauw .............. 514/247 |
| 5,302,606 | A |   | 4/1994  | Spada et al. |
| 5,330,992 | A |   | 7/1994  | Eissenstat et al. |
| 5,792,783 | A |   | 8/1998  | Tang et al. |
| 6,130,238 | A |   | 10/2000 | Tang et al. |
| 6,395,734 | B1|   | 5/2002  | Tang et al. |

FOREIGN PATENT DOCUMENTS

| EP | 0 566 226 B1 | 8/1995 |
| WO | WO 91/15495 A1 | 10/1991 |
| WO | WO 92/20642 A1 | 11/1992 |
| WO | WO 92/22160 A1 | 12/1992 |
| WO | WO 94/03427 A1 | 2/1994 |
| WO | WO 94/10202 A1 | 5/1994 |
| WO | WO 94/14808 A1 | 7/1994 |

OTHER PUBLICATIONS

Cheng et al., "Syntheses of 6-Substituted Truncated Yuehchukene Analogs," Australian Journal of Chemistry, vol. 50(4), p. 349-353 (1997).*
Chen et al., STN International (2006) HCAPLUS Database, Columbus, OH, Accession No. 1997:452077.*

Jellinek et al., "Inhibition of Receptor Binding by High-Affinity RNA Ligands to Vascular Endothelial Growth Factor," *Biochemistry*, 1994, pp. 10450-10456, vol. 33, American Chemical Society.
Kendall et al., "Inhibition of vascular endothelial cell growth factor activity by an endogenously encoded soluble receptor," *Proc. Natl. Acad. Sci. USA*, Nov. 1993, pp. 10705-10709, vol. 90.
Kim et al., "Inhibition of vascular endothelial growth factor-induced angiogenesis suppresses tumour growth *in vivo*,"*Nature*, Apr. 29, 1993, pp. 841-844, vol. 362, No. 6423.
Kinsella et al., "Protein Kinase C Regulates Endothelial Cell Tube Formation on Basement Membrane Matrix, Matrigel," *Experimental Cell Research*, 1992, pp. 56-62, vol. 199, No. 1, Academic Press, Inc.
Mariani et al., "Inhibition of angiogensis by FCE 26806, a potent tyrosine kinase inhibitor," *Proc. Am. Assoc. Cancer Res.*, Mar. 1994, p. 381, vol. 35.
Takano et al., "Inhibition of Angiogenesis by a Novel Diaminoanthraquinone that Inhibits Protein Kinase," *Molecular Biology of the Cell*, Oct. 1993, p. 358a, Abstract #2076, vol. 4.
Wright et al., "Inhibition of Angiogenesis In Vitro and In Ovo With an Inhibitor of Cellular Protein Kinases, MDL 27032," *Journal of Cellular Physiology*, Sep. 1992, pp. 448-457, vol. 152, No. 3.

* cited by examiner

*Primary Examiner*—Golam M. M. Shameem
*Assistant Examiner*—Andrew B. Freistein
(74) *Attorney, Agent, or Firm*—Bryan C. Zielinski; Vincent P. Liptak

(57) ABSTRACT

The present invention relates to certain sulfonamido-substituted geometrically restricted indolinones of the formula:

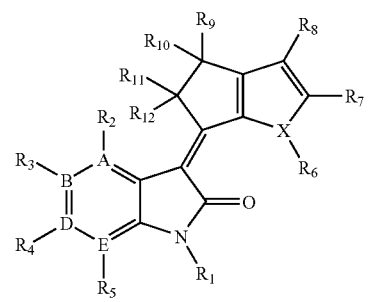

wherein $R_1$–$R_{12}$ and X are variables defined herein.

The sulfonamido-substituted geometrically restricted indolinones of the preferred embodiments of the present invention modulate the activity of protein kinases ("PKs"). The compounds of this invention are therefore useful in treating disorders related to abnormal PK activity.

Pharmaceutical compositions comprising these compounds, methods of treating diseases utilizing pharmaceutical compositions comprising these compounds and methods of preparing them are also disclosed.

4 Claims, No Drawings

US 7,105,562 B2

GEOMETRICALLY RESTRICTED 3-CYCLOPENTYLIDENE-1,3-DIHYDROINDOL-2-ONES AS POTENT PROTEIN TYROSINE KINASE INHIBITORS

FIELD OF THE INVENTION

The present invention relates to certain sulfonamido-substituted geometrically restricted indolinones which modulate the activity of protein kinases ("PKs"). The compounds of this invention are therefore useful in treating disorders related to abnormal PK activity. Pharmaceutical compositions comprising these compounds, methods of treating diseases utilizing pharmaceutical compositions comprising these compounds and methods of preparing them are also disclosed.

BACKGROUND OF THE INVENTION

The following is offered as background information only and is not admitted to be prior art to the present invention.

Protein kinases ("PKs") are enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer).

The PKs can be conveniently broken down into two classes, the protein tyrosine kinases (PTKs) and the serine-threonine kinases (STKs).

One of the prime aspects of PTK activity is their involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger and Ullrich, *Neuron* 9:303–391 (1992), which is incorporated by reference, including any drawings, as if fully set forth herein.

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR, (epithelial growth factor receptor), HER2, HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated α subunits and two β subunits which cross the cell membrane and which contain the tyrosine kinase domain.

Another RTK subfamily is referred to as the platelet derived growth factor receptor ("PDGFR") group, which includes PDGFRα, PDGFRβ, CSFIR, c-kit and flt-3. These receptors consist of glycosylated extracellular domains composed of 5 immunoglobin-like loops and an intracellular domain wherein the tyrosine kinase domain is interrupted by a kinase insert domain.

Another group which, because of its similarity to the PDGFR subfamily, is sometimes subsumed into the latter group is the fetal liver kinase ("flk") receptor subfamily. This group, containing extracellular immunoglobulin loops made up of kinase insert domain-receptor fetal liver kinase-1 (KDR/FLK-1), and fms-like tyrosine kinase 1 (flt-1 and flt-4).

A further member of the tyrosine kinase growth factor receptor family is the fibroblast growth factor ("FGF") receptor subgroup. This group consists of four receptors, FGFR1–4, and many ligands. Although there is considerable alternative splicing, generally the receptors consist of a glycosylated extracellular domain containing 3 immunoglobin-like loops and an intracellular domain in which the tyrosine kinase sequence is interrupted by regions of a kinase insert domain.

Still another member of the tyrosine kinase growth factor receptor family is MET, often referred to as c-Met also known as human hepatocyte growth factor receptor tyrosine kinase (hHGFR). c-Met is thought to play a role in primary tumor growth and metastasis.

A more complete listing of the known RTK subfamilies is described in Plowman et al., *DN&P*, 7(6):334–339 (1994), which is incorporated by reference, including any drawings, as if fully set forth herein.

In addition to the RTKs, there also exists a family of entirely intracellular PTKs called "non-receptor tyrosine kinases" or "cytoplasmic tyrosine kinases." This latter designation, abbreviated "CTK," will be used herein. CTKs do not contain extracellular and transmembrane domains. At present, over 24 CTKs in 11 subfamilies (Src, Frk, Btk, Csk, Abl, Zap70, Fes, Fak, Jak, LIMK and Ack) have been identified. The Src subfamily appear so far to be the largest group of CTKs and includes Src, Yes, Fyn, Lyn, Lck, Blk, Hck, Fgr, and Yrk. For a more detailed discussion of CTKs, see Bolen, *Oncogene*, 8:2025–2031 (1993), which is incorporated by reference, including any drawings, as if fully set forth herein.

The serine/threonine kinases, STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes. The STKs include CDk2, Raf, the ZC family of kinases, the NEK family of kinases, and BUB1.

RTKs, CTKs and STKs have all been implicated in a host of pathogenic conditions including, significantly, cancer. Other pathogenic conditions which have been associated with PTKs include, without limitation, psoriasis, hepatic cirrhosis, diabetes, angiogenesis, fibrosis, restenosis, ocular diseases, rheumatoid arthritis and other inflammatory disorders, immunological disorders such as autoimmune disease, cardiovascular disease such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

In view of the apparent link between PK-related cellular activities and wide variety of human disorders, it is no surprise that a great deal of effort is being expended in an attempt to identify ways to modulate PK activity. Some of these have involved biomimetic approaches using large molecules patterned on those involved in the actual cellular processes (e.g., mutant ligands (U.S. Pat. No. 4,966,849); soluble receptors and antibodies (Application No. WO 94/10202, Kendall and Thomas, *Proc. Nat'l Acad. Sci.*, 90:10705–10709 (1994), Kim, et al., Nature, 362:841–844 (1993)); RNA ligands (Jelinek, et al., *Biochemistry*, 33:10450–56); Takano, et al., *Mol. Bio. Cell*, 4:358A (1993); Kinsella, et al., *Exp. Cell Res.*, 199:56–62 (1992); Wright, et al., *J. Cellular Phys.*, 152:448–57) and tyrosine kinase inhibitors (WO 94/03427; WO 92/21660; WO 91/15495; WO 94/14808; U.S. Pat. No. 5,330,992; Mariani, et al., *Proc. Am. Assoc. Cancer Res.*, 35:2268 (1994)).

In addition to the above, attempts have been made to identify small molecules which act as PK inhibitors. For example, bis-monocylic, bicyclic and heterocyclic aryl compounds (PCT WO 92/20642), vinylene-azaindole derivatives (PCT WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP Application No. 0 566 266 A1), selenaindoles and selenides (PCT WO 94/03427), tricyclic polyhydroxylic compounds (PCT WO 92/21660) and benzylphosphonic acid compounds (PCT WO 91/15495) have all been described as PTK inhibitors useful in the treatment of cancer. However, more effective PTK inhibitors are needed.

SUMMARY OF THE INVENTION

In one aspect, the invention relates to a compound of Formula I:

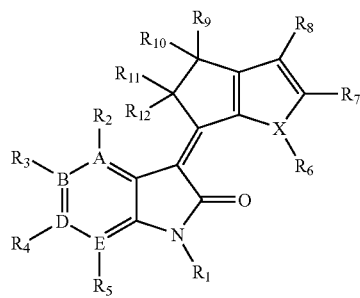

wherein A, B, D and E are each independently selected from the group consisting of carbon and nitrogen such that when A is nitrogen, B and E are carbon and when E is nitrogen and A is carbon, then B is carbon or nitrogen;

wherein when A, B, D or E is nitrogen, $R_2$, $R_3$, $R_4$ or $R_5$ do not exist respectively;

with the proviso that the ring containing A, B, D and E contains no more than two nitrogens;

$R_1$ and $R_6$ are each H;

$R_2$, $R_3$, $R_4$, $R_5$, $R_7$ and $R_8$ are each independently selected from the group consisting of H, alkyl, cycloalkyl, alkenyl, alkynyl, aryl, heteroaryl, trihaloalkyl, heteroalicyclic, hydroxy, alkoxy, aryloxy, mercapto, alkylthio, arylthio, —$SOR_{13}$, —$SO_2R_{13}$, —$SO_2NR_{13}R_{14}$, $R_{14}SO_2N(R_{13})$—, N-trihalomethanesulfonamido, —$C(O)R_{15}$, —$C(O)OR_{15}$, $R_{15}C(O)O$—, cyano, nitro, halo, cyanato, isocyanato, isocyanato, thiocyanato, isothiocyanato, —$OC(O)NR_{13}R_{14}$, $R_{14}OC(O)NR_{13}$—, —$OC(S)NR_{13}R_{14}$, $R_{14}OC(S)NR_{13}$—, —$C(O)NR_{13}R_{14}$, $R_{14}C(O)NR_{13}$— and —$NR_{13}R_{14}$;

$R_2$ and $R_3$ or $R_3$ and $R_4$ or $R_4$ and $R_5$ or $R_7$ and $R_8$ together with the atoms to which they are attached may combine to form a methylenedioxy group, an ethylenedioxy group, an alicyclic ring or a heteroalicyclic ring;

$R_{13}$ and $R_{14}$ are each independently selected from the group consisting of H, alkyl, cycloalkyl, aryl, alkylaryl, arylalkyl, heteroaryl, heteroalicyclic, —$C(O)R_{15}$, acetyl, —$SO_2R_{15}$ and —$(CH_2)_nNR_{13}R_{14}$;

or $R_{13}$ and $R_{14}$ together with the atoms to which they are attached may form a five- or a six-membered heteroalicyclic ring;

$R_{15}$ is selected from the group consisting of H, alkyl, cycloalkyl, aryl, heteroaryl and heteroalicyclic;

$R_9$, $R_{10}$, $R_{11}$, and $R_{12}$ are each independently selected from the group consisting of H, alkyl, cycloalkyl, alkenyl, alkynyl, aryl, heteroaryl, trihaloalkyl, halo, cyano, hydroxy, alkoxy, aryloxy, alkylthio, arylthio, —$SO_2R_{15}$, —$S(O)R_{15}$, —$(CH_{2n}C(O)OR_{15}$, cyanato, isocyanato, thiocyanato, isothiocyanato, —$C(O)NR_{13}R_{14}$, $R_{14}C(O)NR_{13}$— and —$NR_{13}R_{14}$;

n is an integer from 0 to 20;

X is selected from the group consisting of nitrogen, oxygen, and sulfur; and wherein when X is oxygen or sulfur, then $R_6$ does not exist;

or a prodrug or pharmaceutically acceptable salt thereof.

In preferred embodiments, the invention relates to compounds of Formula I, wherein A, B, D and E are carbon. In other preferred embodiments, the invention relates to compounds of Formula I, wherein A, B, D and E are carbon and X is nitrogen. In still other preferred embodiments, the invention relates to compounds of Formula I, wherein $R_2$, $R_3$, $R_4$, $R_5$, $R_7$ and $R_8$ are each independently selected from the group consisting of H, alkyl, aryl, hydroxy, alkoxy, —$SOR_{13}$, —$SO_2R_{13}$, —$SO_2NR_{13}R_{14}$, —$C(O)OR_{15}$, halo and —$C(O)NR_{13}R_{14}$.

In other preferred embodiments, the invention relates to compounds of Formula i, wherein $R_2$, $R_3$, $R_4$, $R_5$, $R_7$ and $R_8$ are each independently selected from the group consisting of H, alkyl, aryl, hydroxy, alkoxy, —$SOR_{13}$, —$SO_2R_{13}$, —$SO_2NR_{13}R_{14}$, —$C(O)OR_{15}$, halo and —$C(O)NR_{13}R_{14}$ and A, B, D and E are carbon. In still other preferred embodiments, the invention relates to a compound of Formula I, wherein $R_2$, $R_3$, $R_4$, $R_5$, $R_7$ and $R_8$ are each independently selected from the group consisting of H, alkyl, aryl, hydroxy, alkoxy, —$SOR_{13}$, —$SO_2R_{13}$, —$SO_2NR_{13}R_{14}$, —$C(O)OR_{15}$, halo and —$C(O)NR_{13}R_{14}$; A, B, D and E are carbon; and X is nitrogen.

In yet other preferred embodiments, the invention relates to a compound of Formula I which is:

2-methyl-6-[2-oxo-1,2-dihydro-indol-(3Z)-ylidene]1,4,5,6-tetrahydro-cyclopenta[b]pyrrole-3-carboxylic acid ethyl ester;

6-[5-(2,6-dichloro-phenylmethanesulfonyl)-2-oxo-1,2-dihydro-indol-(3Z)-ylidene]-2-methyl-1,4,5,6-tetrahydro-cyclopenta[b]pyrrole-3-carboxylic acid ethyl ester;

2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid ethyl ester;

3-[2-methyl-4,5-dihydro-1H-cyclopenta[b]pyrrol(6Z)-ylidene]-2-oxo-2,3-dihydro-1H-indole-5-sulfonic acid methylamide;

2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid;

6-[5-methanesulfonyl-2-oxo-1,2-dihydro-indol-(3Z)-ylidene]-2-methyl-1,4,5,6-tetrahydro-cyclopenta[b]pyrrole-3-carboxylic acid ethyl ester;

6-[5-dimethylsulfamoyl-2-oxo-1,2-dihydro-indol(3Z)-ylidene]-2-methyl-1,4,5,6-tetrahydro-cyclopenta[b]pyrrole-3-carboxylic acid ethyl ester;

6-[5-isopropylsulfamoyl-2-oxo-1,2-dihydro-indol-(3Z)-ylidene]-2-methyl-1,4,5,6-tetrahydro-cyclopenta[b]pyrrole-3-carboxylic acid ethyl ester;

6-[5-ethanesulfonyl-2-oxo-1,2-dihydro-indol-(3Z)-ylidene]-2-methyl-1,4,5,6-tetrahydro-cyclopenta[b]pyrrole-3-carboxylic acid ethyl ester;

2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid (2-hydroxy-3-pyrrolidin-1-yl-propyl)-amide;

2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid (3-cyclopropylamino-2-hydroxy-propyl)-amide;

2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid (2-dimethylamino-ethyl)-amide;

3-[2-methyl-3-((R)-2-pyrrolidin-1-ylmethyl-pyrrolidine-1-carbonyl)-4,5-dihydro-1H-cyclopenta[b]pyrrol-(6Z)-ylidene]-2-oxo-2,3-dihydro-1H-indole-5-sulfonic acid methylamide;

2-methyl-6-[2-oxo-5-sulfamoyl-1,2-dihydro-indol-(3Z)-ylidene]-1,4,5,6-tetrahydro-cyclopenta[b]pyrrole-3-carboxylic acid ethyl ester;

3-[3-methanesulfonyl-2-methyl-4,5-dihydro-1H-cyclopenta[b]pyrrol-(6Z)-ylidene]-2-oxo-2,3-dihydro-1H-indole-5-sulfonic acid methylamide;

{6-methoxy-3-[5-methylsulfamoyl-2-oxo-1,2-dihydro-indol-(3Z)-ylidene]-indan-1-yl}-acetic acid;

5-fluoro-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one;

6-methoxy-3-[2-methyl-3-((S)-2-pyrrolid in-1-ylmethyl-pyrrolidine-1-carbonyl)-4,5-dihydro-1H-cyclopenta[b]pyrrol-(6Z)-ylidene]-1,3-dihydro-indol-2-one;

4-methoxy-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one;

7-chloro-3-[2-methyl-3-((S)-2-pyrrolidin-1-ylmethyl-pyrrolidine-1-carbonyl)4,5-dihydro-1H-cyclopenta[b]pyrrol-(6Z)-ylidene]-1,3-dihydro-indol-2-one;

3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-pyrrolo[2,3-b]pyridin-2-one; and 6-(4-methoxy-phenyl)-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one;

or a prodrug or pharmaceutically acceptable salt thereof.

In another aspect, the invention relates to a compound of the Formula II:

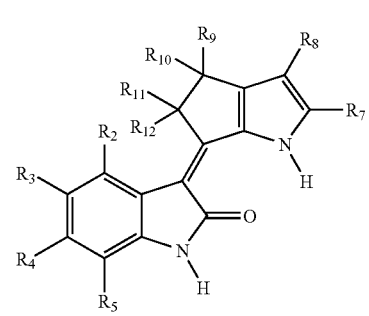

II $R_2$, $R_3$, $R_4$, $R_5$, $R_7$ and $R_8$ are each independently selected from the group consisting of H, alkyl, cycloalkyl, alkenyl, alkynyl, aryl, heteroaryl, trihaloalkyl, heteroalicyclic, hydroxy, alkoxy, aryloxy, mercapto, alkylthio, arylthio, —$SOR_{13}$, —$SO_2R_{13}$, —$SO_2NR_{13}R_{14}$, $R_{14}SO_2N(R_{13})$—, N-trihalomethanesulfonamido, —$C(O)R_{15}$, —$C(O)OR_{15}$, $R_{15}C(O)O$—, cyano, nitro, halo, cyanato, isocyanato, isocyanato, thiocyanato, isothiocyanato, —$OC(O)NR_{13}R_{14}$, $R_{14}OC(O)NR_{13}$—, —$OC(S)NR_{13}R_{14}$, $R_{14}OC(S)NR_{13}$—, —$C(O)NR_{13}R_{14}$, $R_{14}C(O)NR_{13}$— and —$NR_{13}R_{14}$;

$R_2$ and $R_3$ or $R_3$ and $R_4$ or $R_4$ and $R_5$ or $R_7$ and $R_8$ together with the atoms to which they are attached may combine to form a methylenedioxy group, an ethylenedioxy group, an alicyclic ring or a heteroalicyclic ring;

$R_{13}$ and $R_{14}$ are each independently selected from the group consisting of H, alkyl, cycloalkyl, aryl, alkylaryl, arylalkyl, heteroaryl, heteroalicyclic, —$C(O)R_{15}$, acetyl, —$SO_2R_{15}$ and —$(CH_2)_nNR_{13}R_{14}$;

or $R_{13}$ and $R_{14}$ together with the atoms to which they are attached may form a five- or six-membered heteroalicyclic ring;

wherein $R_{15}$ is selected from the group consisting of H, alkyl, cycloalkyl, aryl, heteroaryl and heteroalicyclic;

$R_9$, $R_{10}$, $R_{11}$, and $R_{12}$ are each independently selected from the group consisting of H, alkyl, cycloalkyl, alkenyl, alkynyl, aryl, heteroaryl, trihaloalkyl, halo, cyano, hydroxy, alkoxy, aryloxy, alkylthio, arylthio, —$SO_2R_{15}$, —$S(O)R_{15}$, —$(CH_2)_nC(O)OR_{15}$, cyanato, isocyanato, thiocyanato, isothiocyanato, —$C(O)NR_{13}R_{14}$, $R_{14}C(O)NR_{13}$— and —$NR_{13}R_{14}$; and n is an integer from 0 to 20;

or a prodrug or pharmaceutically acceptable salt thereof.

In a preferred embodiment, the invention relates to a compound of Formula II, wherein $R_2$, $R_3$, $R_4$, $R_5$, $R_7$ and $R_8$ are each independently selected from the group consisting of H, alkyl, aryl, hydroxy, alkoxy, —$SOR_{13}$, —$SO_2R_{13}$, —$SO_2NR_{13}R_{14}$, —$C(O)OR_{15}$, halo and —$C(O)NR_{13}R_{14}$.

In another preferred embodiment, the compound of Formula II is:

2-methyl-6-[2-oxo-1,2-dihydro-indol-(3Z)-ylidene]1,4,5,6-tetrahydro-cyclopenta[b]pyrrole-3-carboxylic acid ethyl ester;

6-[5-(2,6-dichloro-phenylmethanesulfonyl)-2-oxo-1,2-dihydro-indol-(3Z)-ylidene]-2-methyl-1,4,5,6-tetrahydro-cyclopenta[b]pyrrole-3-carboxylic acid ethyl ester;

2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid ethyl ester;
3-[2-methyl-4,5-dihydro-1H-cyclopenta[b]pyrrol(6Z)-ylidene]-2-oxo-2,3-dihydro-1H-indole-5-sulfonic acid methylamide;
2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid;
6-[5-methanesulfonyl-2-oxo-1,2-dihydro-indol-(3Z)-ylidene]-2-methyl-1,4,5,6-tetrahydro-cyclopenta[b]pyrrole-3-carboxylic acid ethyl ester;
6-[5-dimethylsulfamoyl-2-oxo-1,2-dihydro-indol(3Z)-ylidene]-2-methyl-1,4,5,6-tetrahydro-cyclopenta[b]pyrrole-3-carboxylic acid ethyl ester;
6-[5-isopropylsulfamoyl-2-oxo-1,2-dihydro-indol-(3Z)-ylidene]-2-methyl-1,4,5,6-tetrahydro-cyclopenta[b]pyrrole-3-carboxylic acid ethyl ester;
6-[5-ethanesulfonyl-2-oxo-1,2-dihydro-indol-(3Z)-ylidene]-2-methyl-1,4,5,6-tetrahydro-cyclopenta[b]pyrrole-3-carboxylic acid ethyl ester;
2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid (2-hydroxy-3-pyrrolidin-1-yl-propyl)-amide;
2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid (3-cyclopropylamino-2-hydroxy-propyl)-amide;
2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid (2-dimethylamino-ethyl)-amide;
3-[2-methyl-3-((R)-2-pyrrolidin-1-ylmethyl-pyrrolidine-1-carbonyl)4,5-dihydro-1H-cyclopenta[b]pyrrol-(6Z)-ylidene]-2-oxo-2,3-dihydro-1H-indole-5-sulfonic acid methylamide;
2-methyl-6-[2-oxo-5-sulfamoyl-1,2-dihydro-indol-(3Z)-ylidene]-1,4,5,6-tetrahydro-cyclopenta[b]pyrrole-3-carboxylic acid ethyl ester;
3-[3-methanesulfonyl-2-methyl4, 5-dihydro-1H-cyclopenta[b]pyrrol-(6Z)-ylidene]-2-oxo-2,3-dihydro-1H-indole-5-sulfonic acid methylamide;
{6-methoxy-3-[5-methylsulfamoyl-2-oxo-1,2-dihydro-indol-(3Z)-ylidene]-indan-1-yl}-acetic acid;
5-fluoro-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one;
6-methoxy-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one;
4-methoxy-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one;
7-chloro-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one;
3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-pyrrolo[2,3-b]pyridin-2-one; and
6-(4-methoxy-phenyl)-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one;
or a prodrug or pharmaceutically acceptable salt thereof.

In another aspect, the invention relates to a pharmaceutical composition comprising a compound of Formula I or II, or a prodrug or a pharmaceutically acceptable salt of a compound of Formula I or II and a pharmaceutically acceptable carrier or excipient.

In yet another aspect, the invention relates to a method for the modulation of the catalytic activity of a protein kinase comprising contacting said protein kinase with a compound of Formula I and II or a prodrug or a pharmaceutically acceptable salt of a compound of Formula I and II. In a preferred embodiment, the protein kinase is selected from the group consisting of a receptor tyrosine kinase, a non-receptor tyrosine kinase and a serine-threonine kinase.

In still another aspect, the invention relates to a method for treating or preventing a protein kinase related disorder in an organism comprising administering a therapeutically effective amount of a pharmaceutical composition comprising a compound of Formula I and II or a prodrug or a pharmaceutically acceptable salt of a compound of Formula I and II and a pharmaceutically acceptable carrier or excipient to the organism. In a preferred embodiment, the protein kinase related disorder is selected from the group consisting of a receptor tyrosine kinase related disorder, a non-receptor tyrosine kinase related disorder and a serine-threonine kinase related disorder. In another preferred embodiment, the protein kinase related disorder is selected from the group consisting of a PDGFR related disorder and a flk related disorder. In a preferred embodiment, the protein kinase related disorder is a cancer selected from the group consisting of squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, glioma, colorectal cancer, genitourinary cancer and gastrointestinal cancer. In another preferred embodiment, the protein kinase related disorder is selected from the group consisting of diabetes, an autoimmune disorder, a hyperproliferation disorder, restenosis, fibrosis, psoriasis, von Heppel-Lindau disease, osteoarthritis, rheumatoid arthritis, angiogenesis, an inflammatory disorder, an immunological disorder and a cardiovascular disorder. In a preferred embodiment, the organism is a human.

DETAILED DESCRIPTION OF THE PREFERRED EMBODIMENTS

A family of novel sulfonamido-substituted geometrically restricted indolinones have been discovered which exhibit PK modulating ability and have a ameliorating effect against disorders related to abnormal PK activity.

The compounds presented herein are exemplary only and are not to be construed as limiting the scope of this invention in any manner.

In another aspect, the invention is directed to a pharmaceutical composition comprising one or more compounds of the Formula (I), or a pharmaceutically acceptable salt thereof and a pharmaceutically acceptable excipient.

It is also an aspect of this invention that a compound described herein, or its salt, might be combined with other chemotherapeutic agents for the treatment of the diseases and disorders discussed above. For instance, a compound or salt of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Likewise a compound or salt of this invention might be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

A compound or salt of this invention might also be expected to prove efficacious in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound or salt of this invention might be expected to have a beneficial effect used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors (such as anastrozole.

Finally, the combination of a compound of this invention might be expected to be particularly effective in combination with mitoxantrone or paclitaxel for the treatment of solid tumor cancers or leukemias such as, without limitation, acute myelogenous (non-lymphocytic) leukemia.

The above method can be carried out in combination with a chemotherapeutic agent selected from the group consisting of mitotic inhibitors, alkylating agents, antimetabolites, cell cycle inhibitors, enzymes, topoisomerase inhibitors, biological response modifiers, anti-hormones, antiangiogenic agents such as MMP-2, MMP-9 and COX-2 inhibitors, and anti-androgens.

Examples of useful COX-II inhibitors include Vioxx™, CELEBREX™ (alecoxib), valdecoxib, paracoxib, rofecoxib, and Cox 189. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21,1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference.

Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP4, MMP-5, MMP-6, MMP-7, MMP-8, MMP-10, MMP-11, MMP-12, and MMP-13). Some specific examples of MMP inhibitors useful in the present invention are AG-3340, RO 32–3555, RS 13–0830, and the compounds recited in the following list:

3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R, 3R) 1-[4-(2-chloro4-fluoro-benzyloxy)-benzenesulfonyl]-3-hydroxy-3-methyl-piperid ine-2-carboxylic acid hydroxyamide; 4-[4-(4-fluoro-phenoxy)-benzenesulfonylamino]-tetrahydro-pyran4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran4-carboxylic acid hydroxyamide; (R) 3-[4-(4-chloro-phenoxy)-benzenesulfonylamino]-tetrahydro-pyran-3-carboxylic acid hydroxyamide; (2R, 3R) 1-[4-(4-fluoro-2-methyl-benzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1] octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

Other anti-angiogenesis agents, including other COX-II inhibitors and other MMP inhibitors, can also be used in the present invention.

Compounds of the Formula (I) can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

These and other EGFR-inhibiting agents can be used in the present invention.

VEGF inhibitors, for example SU-5416, SU 11248, SU-6668 (Sugen Inc. of South San Francisco, Calif., USA), can also be combined with a compound of the Formula (I). VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 01/60814, WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with a compound of the Formula (I) for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with compounds of the Formula (I), in accordance with the present invention.

Compounds of the Formula (I) can also be used with other agents useful in treating cancer, including, but not limited to, agents capable of enhancing antitumor immune responses, such as CTLA4 (cytotoxic lymphocite antigen 4) antibodies, and other agents capable of blocking CTLA4; and antiproliferative agents such as other farnesyl protein transferase inhibitors, for example the farnesyl protein transferase inhibitors described in the references cited in the "Background" section, of U.S. Pat. No. 6,258,824 B1. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

The above method can be also be carried out in combination with radiation therapy, wherein the amount of a compound of the Formula (I) in combination with the radiation therapy, is effective in treating the above diseases. The level of radiation therapy administered may be reduced to a sub-efficacy dose when administered in combination with the compounds of the preferred embodiments of the present invention.

Techniques for administering radiation therapy are known in the art, and these techniques can be used in the combination therapy described herein. The administration of the compound of the invention in this combination therapy can be determined as described herein.

Another aspect of the invention is directed to the use of compounds of the Formula I or II in the preparation of a medicament, which is useful in the treatment of a disease mediated by abnormal protein kinase activity. In one aspect, a preferred embodiment of the present invention relates to the use of compounds of Formula I and II in the preparation of a medicament, which is useful in the treatment of a disease mediated by abnormal protein kinase activity.

"Pharmaceutically acceptable salt" or "pharmaceutically acceptable salt thereof" refer to those salts which retain the biological effectiveness and properties of the free bases and which are obtained by reaction with inorganic or organic acids, such as hydrochloric acid, hydrobromic acid, hydroiodic acid, sulfuric acid, nitric acid, phosphoric acid, methanesulfonic acid, ethanesulfonic acid, p-toluenesulfonic acid, salicylic acid, acetic acid, benzenesulfonic acid (besylate), benzoic acid, camphorsulfonic acid, citric acid, fumaric acid, gluconic acid, glutamic acid, isethionic acid, lactic acid, maleic acid, malic acid, mandelic acid, mucic acid, pamoic acid, pantothenic acid, succinic acid, tartaric acid, and the like.

A "pharmaceutical composition" refers to a mixture of one or more of the compounds described herein, or physiologically acceptable salts thereof, with other chemical components, such as physiologically acceptable carriers and excipients. The purpose of a pharmaceutical composition is to facilitate administration of a compound to an organism.

As used herein, a "physiologically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives (including microcrystalline cellulose), gelatin, vegetable oils, polyethylene glycols, diluents, granulating agents, lubricants, binders, disintegrating agents, and the like.

"Alkyl" refers to a saturated aliphatic hydrocarbon including straight chain, branched chain or cyclic groups. Preferably, the alkyl group has 1 to 20 carbon atoms (whenever a numerical range; e.g., "1–20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, each substituent group is preferably one or more individually selected from halogen, -hydroxy, —COR', —COOR', OCOR', —CONRR', —RNCOR', —NRR', —CN, —$NO_2$, —$CZ_3$, —SR', —SOR', —$SO_2$R', —$SO_2$OR', —$SO_2$NRR', thiocarbonyl, —$RNSO_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' are independently H, alkyl, or aryl, wherein alkyl or aryl may be further substituted with halogen, $(CH_2)_nN(R")_2$, $(CH_2)_nCO_2R"$, $(CH_2)_nOR"$, $(CH_2)_nOC(O)R"$, alkoxycarbonyl, aryloxycarbonyl, aminocarbonyl, a heteroalicyclic ring, aryl, alkoxy, —$OCZ_3$, aryloxy, $C(O)NH_2$ or heteroaryl. R" is H, alkyl or aryl. n is 0–3.

"Alkenyl" refers to an aliphatic hydrocarbon having at least one carbon-carbon double bond, including straight chain, branched chain or cyclic groups having at least one carbon-carbon double bond. Preferably, the alkenyl group has 2 to 20 carbon atoms (whenever a numerical range; e.g., "2–20", is stated herein, it means that the group, in this case the alkenyl group, may contain 2 carbon atoms, 3 carbon atoms, etc. up to and including 20 carbon atoms). More preferably, it is a medium size alkenyl having 2 to 10 carbon atoms. Most preferably, it is a lower alkenyl having 2 to 6 carbon atoms. The alkenyl group may be substituted or unsubstituted. When substituted, each substituent group is preferably one or more individually selected from halogen, -hydroxy, —COR', —COOR', OCOR', —CONRR', —RNCOR', —NRR', —CN, —$NO_2$, —$CZ_3$, —SR', —SOR', —$SO_2$R', —$SO_2$OR', —$SO_2$NRR', thiocarbonyl, —$RNSO_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

"Alkynyl" refers to an aliphatic hydrocarbon having at least one carbon-carbon triple bond, including straight chain, branched chain or cyclic groups having at least one carbon-carbon triple bond. Preferably, the alkenyl group has 2 to 20 carbon atoms (whenever a numerical range; e.g., "2–20", is stated herein, it means that the group, in this case the alkynyl group, may contain 2 carbon atoms, 3 carbon atoms, etc. up to and including 20 carbon atoms). More preferably, it is a medium size alkynyl having 2 to 10 carbon atoms. Most preferably, it is a lower alkynyl having 2 to 6 carbon atoms. The alkynyl group may be substituted or unsubstituted. When substituted, each substituent group is preferably one or more individually selected from halogen, -hydroxy, —COR', —COOR', OCOR', —CONRR', —RNCOR', —NRR', —CN, —$NO_2$, —$CZ_3$, —SR', —SOR', —$SO_2$R', —$SO_2$OR', —$SO_2$NRR', thiocarbonyl, —$RNSO_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

A "cycloalkyl" or an "alicyclic" group refers to an all-carbon monocyclic or fused ring (i.e., rings which share an adjacent pair of carbon atoms) group wherein one or more of the rings does not have a completely conjugated pi-electron system. Examples, without limitation, of cycloalkyl groups are cyclopropane, cyclobutane, cyclopentane, cyclopentene, cyclohexane, adamantane, cyclohexadiene, cycloheptane and, cycloheptatriene. A cycloalkyl group may be substituted or unsubstituted. When substituted, each substituent group is preferably one or more individually selected from halogen, -hydroxy, —COR', —COOR', OCOR', —CONRR', —RNCOR', —NRR', —CN, —$NO_2$, —$CZ_3$, —SR', —SOR', —$SO_2$R', —$SO_2$OR', —$SO_2$NRR', thiocarbonyl, —$RNSO_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, each substituted group is preferably one or more selected halogen, hydroxy, alkoxy, aryloxy,—COR', —COOR', OCOR', —CONRR', —RNCOR', —NRR', —CN, —$NO_2$, —$CZ_3$, —$OCZ_3$, —SR', —SOR', —$SO_2$R', —$SO_2$OR', —$SO_2$NRR', thiocarbonyl, —$RNSO_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, each substituted group is preferably one or more selected from halogen, -hydroxy, —COR', —COOR', OCOR', —CONRR', —RNCOR', —NRR', —CN, —$NO_2$, —$CZ_3$, —SR', —SOR', —$SO_2$R', —$SO_2$OR', —$SO_2$NRR', thiocarbonyl, —$RNSO_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl, where Z is halogen. Wherein R and R' are defined herein.

A "heteroalicyclic ring" or "heteroalicycle" group refers to a monocyclic or fused ring group having in the ring(s) one or more atoms selected from the group consisting of nitrogen, oxygen and sulfur. The rings may also have one or more double bonds. However, the rings may not have a completely conjugated pi-electron system. The heteroalicyclic ring may be substituted or unsubstituted. The heteroalicyclic ring may contain one or more oxo groups. When substituted, the substituted group(s) is preferably one or more selected halogen, hydroxy, —COR', —COOR', OCOR', —CON RR', —RNCOR', —NRR', —CN, —$NO_2$, —$CZ_3$, —SR', —SOR', —$SO_2$R', —$SO_2$O', —$SO_2$NRR', thiocarbonyl, —$RNSO_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

Z refers to a halogen group selected from the group consisting of fluorine, chlorine, bromine and iodine.

A "hydroxy" group refers to an —OH group.

An "alkoxy" group refers to both an —O-alkyl and an —O-cycloalkyl group, as defined herein.

An "alkoxycarbonyl" refers to a —C(O)—OR.

An "aminocarbonyl" refers to a —C(O)—NRR'.

An "aryloxycarbonyl" refers to —C(O)-Oaryl.

An "aryloxy" group refers to both an —O-aryl and an —O-heteroaryl group, as defined herein.

An "arylalkyl" group refers to -alkyl-aryl, where alkyl and aryl are defined herein.

An "alkylaryl," group refers to -aryl-alkyl, where alkyl and aryl and defined herein.

An "arylsulfonyl" group refers to a —SO$_2$-aryl.

An "alkylsulfonyl" group refer to a —SO$_2$-alkyl.

A "heteroaryloxyl" group refers to a heteroaryl-O— group with heteroaryl as defined herein.

A "heteroalicycloxy" group refers to a heteroalicyclic-O— group with heteroalicyclic as defined herein.

A "carbonyl" group refers to a —C(=O)—R.

An "aldehyde" group refers to a carbonyl group where R is hydrogen.

A "thiocarbonyl" group refers to a —C(=S)—R group.

A "trihalomethanecarbonyl" group refers to a Z$_3$C—C(O)— group.

A "C-carboxyl" group refers to a —C(O)O—R groups.

An "O-carboxyl" group refers to a R—C(O)O— group.

A "carboxylic acid" group refers to a C-carboxyl group in which R is hydrogen.

A "halo" or "halogen" group refers to fluorine, chlorine, bromine or iodine.

A "trihalomethyl" group refers to a —CZ$_3$ group.

A "trihalomethanesulfonyl" group refers to a Z$_3$CS(O)$_2$ group.

A "trihalomethanesulfonamido" group refers to a Z$_3$CS(O)$_2$NR— group.

A "sulfinyl" group refers to a —S(O)—R group.

A "sulfonyl" group refers to a —S(O)$_2$R group.

An "S-sulfonamido" group refers to a —S(O)$_2$NRR' group.

An "N-Sulfonamido" group refers to a —NR—S(O)$_2$R group.

An "O-carbamyl" group refers to a —OC(O)NRR' group.

An "N-carbamyl" group refers to a ROC(O)NR— group.

An "O-thiocarbamyl" group refers to a —OC(S)NRR' group.

An "N-thiocarbamyl" group refers to a ROC(S)NR'— group.

An "amino" group refers to an —NH$_2$ or an —NRR' group.

A "C-amido" group refers to a —C(O)NRR' group.

An "N-amido" group refers to a R'C(O)NR— group.

A "nitro" group refers to a —NO$_2$ group.

A "cyano" group refers to a —CN group.

A "silyl" group refers to a —Si(R)$_3$ group.

A "phosphonyl" group refers to a —P(=O)(OR)$_2$ group.

An "aminoalkyl" group refers to an -alkylNRR' group.

An "alkylaminoalkyl" group refers to an -alkyl-NR-alkyl group.

A "dialkylamionalkyl" group refers to an -alkyl-N-(alkyl)$_2$ group.

A "perfluoroalkyl group" refers to an alkyl group where all of the hydrogen atoms have been replaced with fluorine atoms.

The definitions of R$_1$—R$_{12}$, X, R, R' and R" are defined in the present specification.

Compounds that have the same molecular formula but differ in the nature or sequence of bonding of their atoms or the arrangement of their atoms in space are termed "isomers". Isomers that differ in the arrangement of their atoms in space are termed "stereoisomers."

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The compounds of Formula I or II may exhibit the phenomena of tautomerism and structural isomerism. For example, the compounds described herein may adopt an E or a Z configuration about any double bond in the molecule. This invention encompasses any tautomeric or structural isomeric form and mixtures thereof which possess the ability to modulate RTK, CTK and/or STK activity and is not limited to any one tautomeric or structural isomeric form.

A "pharmaceutical composition" refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism.

The compound of Formula I and II may also act as a prodrug. A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but then is metabolically hydrolyzed to the carboxylic acid, the active entity, once inside the cell where water solubility is beneficial.

A further example of a prodrug might be a short polypeptide, for example, without limitation, a 2–10 amino acid polypeptide, bonded through a terminal amino group to a carboxy group of a compound of this invention wherein the polypeptide is hydrolyzed or metabolized in vivo to release the active molecule. The prodrugs of a compound of Formula I or II are within the scope of this invention.

Additionally, it is contemplated that a compound of Formula I and II would be metabolized by enzymes in the body of the organism such as a human being to generate a metabolite that can modulate the activity of the protein kinases. Such metabolites are within the scope of the present invention.

As used herein, a "physiologically/pharmaceutically acceptable carrier" refers to a carrier or diluent that does not cause significant irritation to an organism and does not abrogate the biological activity and properties of the administered compound.

An "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts which retain the biological effectiveness and properties of the parent compound. Such salts include:

(1) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"PK" refers to receptor protein tyrosine kinase (RTKs), non-receptor or "cellular" tyrosine kinase (CTKs) and serine-threonine kinases (STKs).

"Method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

"Modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

"Catalytic activity" refers to the rate of phosphorylation of tyrosine under the influence, direct or indirect, of RTKs and/or CTKs or the phosphorylation of serine and threonine under the influence, direct or indirect, of STKs.

"Contacting" refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium.

"In vivo" refers to procedures performed within a living organism such as, without limitation, a mouse, rat or rabbit.

"PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

"Treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

"Organism" refers to any living entity comprised of at least one cell. A living organism can be as simple as, for example, a single eukariotic cell or as complex as a mammal, including a human being.

"Therapeutically effective amount" refers to that amount of the compound being administered which will relieve to some extent one or more of the symptoms of the disorder being treated. In reference to the treatment of cancer, a therapeutically effective amount refers to that amount which has the effect of:

(1) reducing the size of the tumor;

(2) inhibiting (that is, slowing to some extent, preferably stopping) tumor metastasis;

(3) inhibiting to some extent (that is, slowing to some extent, preferably stopping) tumor growth, and/or, (4) relieving to some extent (or, preferably, eliminating) one or more symptoms associated with the cancer.

"Monitoring" means observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art.

The above-referenced effect is selected from a change or an absence of change in a cell phenotype, a change or absence of change in the catalytic activity of the protein kinase or a change or absence of change in the interaction of the protein kinase with a natural binding partner in a final aspect of this invention.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

"Natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

Indications

The PKs whose catalytic activity is modulated by the compounds of this invention include protein tyrosine kinases of which there are two types, receptor tyrosine kinases (RTKS) and cellular tyrosine kinases (CTKs), and serine-threonine kinases (STKs). RTK mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects on the extracellular microenvironment, etc.). See, Schlessinger and Ullrich, 1992, *Neuron* 9:303–391.

It has been shown that tyrosine phosphorylation sites on growth factor receptors function as high-affinity binding sites for SH2 (src homology) domains of signaling molecules. Fantl et al., 1992, *Cell* 69:413–423, Songyang et al., 1994, *Mol. Cell. Biol.* 14:2777–2785), Songyang et al., 1993, *Cell* 72:767–778, and Koch et al., 1991, *Science* 252:668–678. Several intracellular substrate proteins that associate with RTKs have been identified. They may be divided into two principal groups: (1) substrates that have a catalytic domain, and (2) substrates which lack such domain but which serve as adapters and associate with catalytically active molecules. Songyang et al., 1993, *Cell* 72:767–778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, *Cell* 72:767–778. These observations suggest that the function of each RTK is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

STKs, being primarily cytosolic, affect the internal biochemistry of the cell, often as a down-line response to a PTK event. STKs have been implicated in the signaling process which initiates DNA synthesis and subsequent mitosis leading to cell proliferation.

Thus, PK signal transduction results in, among other responses, cell proliferation, differentiation, growth and metabolism. Abnormal cell proliferation may result in a wide array of disorders and diseases, including the development of neoplasia such as carcinoma, sarcoma, glioblastoma and hemangioma, disorders such as leukemia, psoriasis, arteriosclerosis, arthritis and diabetic retinopathy and other disorders related to uncontrolled angiogenesis and/or vasculogenesis.

A precise understanding of the mechanism by which the compounds of this invention inhibit PKs is not required in order to practice the present invention. However, while not hereby being bound to any particular mechanism or theory, it is believed that the compounds interact with the amino acids in the catalytic region of PKs. The compounds disclosed herein may thus have utility as in vitro assays for PKs as well as exhibiting in vivo therapeutic effects through interaction with PKs.

Additionally, the compounds of the present invention provide a therapeutic approach to the treatment of many kinds of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia are also contemplated by this invention. Indications may include, but are not limited to brain cancers, bladder cancers, ovarian cancers, gastric cancers, pancreas cancers, colon cancers, blood cancers, lung cancers and bone cancers.

Further examples, without limitation, of the types of disorders related to inappropriate PK activity that the compounds described herein may be useful in preventing, treating and studying, are cell proliferative disorders, fibrotic disorders and metabolic disorders.

Cell proliferative disorders, which may be prevented, treated or further studied by the present invention include cancer, blood vessel proliferative disorders and mesangial cell proliferative disorders.

Blood vessel proliferative disorders refer to disorders related to abnormal vasculogenesis (blood vessel formation) and angiogenesis (spreading of blood vessels). While vasculogenesis and angiogenesis play important roles in a variety of normal physiological processes such as embryonic development, corpus luteum formation, wound healing and organ regeneration, they also play a pivotal role in cancer development where they result in the formation of new capillaries needed to keep a tumor alive. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness.

Two structurally related RTKs have been identified to bind VEGF with high affinity: the fms-like tyrosine 1 (flt-I) receptor (Shibuya et al., 1990, *Oncogene*, 5:519–524; De Vries et al., 1992, *Science*, 255:989–991) and the KDR/FLK-1 receptor, also known as VEGF-R2. Vascular endothelial growth factor (VEGF) has been reported to be an endothelial cell specific mitogen with in vitro endothelial cell growth promoting activity. Ferrara & Henzel, 1989, *Biochein. Biophys. Res. Comm.*, 161:851–858; Vaisman et al., 1990, *J. Biol. Chem.*, 265:19461–19566. Information set forth in U.S. application Ser. Nos. 08/193,829, 08/038,596 and 07/975,750, strongly suggest that VEGF is not only responsible for endothelial cell proliferation, but also is the prime regulator of normal and pathological angiogenesis. See generally, Klagsburn & Soker, 1993, *Current Biology*, 3(10)699–702; Houck, et al., 1992, *J. Biol. Chem.*, 267: 26031–26037.

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman & Shing, 1992, *J. Biological Chem.*, 267(16):10931–34. Uncontrolled vasculogenesis and/or angiogenesis has been associated with diseases such as diabetes as well as with malignant solid tumors that rely on vascularization for growth. Klagsburn & Soker, 1993, *Current Biology*, 3(10):699–702; Folkham, 1991, *J. Natl. Cancer Inst.*, 82:4–6; Weidner, et al., 1991, *New Enql. J. Med.*, 324:1–5.

The surmised role of VEGF in endothelial cell proliferation and migration during angiogenesis and vasculogenesis indicates an important role for the KDR/FLK-1 receptor in these processes. Diseases such as diabetes mellitus (Folkman, 198, in XI$^{th}$ *Congress of Thrombosis and Haemostasis* (Verstraeta, et al., eds.), pp. 583–596, Leuven University Press, Leuven) and arthritis, as well as malignant tumor growth may result from uncontrolled angiogenesis. See e.g., Folkman, 1971, *N. Enql. J. Med.*, 285:1182–1186. The receptors to which VEGF specifically binds are an important and powerful therapeutic target for the regulation and modulation of vasculogenesis and/or angiogenesis and a variety of severe diseases which involve abnormal cellular growth caused by such processes. Plowman, et al., 1994, *DN&P*, 7(6):334–339. More particularly, the KDR/FLK-1 receptor's highly specific role in neovascularization make it a choice target for therapeutic approaches to the treatment of cancer and other diseases which involve the uncontrolled formation of blood vessels.

Thus, the present invention provides compounds that regulate, modulate and/or inhibit vasculogenesis and/or angiogenesis by affecting the enzymatic activity of the KDR/FLK-1 receptor and interfering with the signal transduced by KDR/FLK-1. Thus the present invention provides a therapeutic approach to the treatment of many kinds of solid tumors including, but not limited to, glioblastoma, melanoma and Kaposi's sarcoma, and ovarian, lung, mammary, prostate, pancreatic, colon and epidermoid carcinoma. In addition, data suggests the administration of compounds which inhibit the KDR/Flk-1 mediated signal transduction pathway may also be used in the treatment of hemangioma, restenois and diabetic retinopathy.

Furthermore, this invention relates to the inhibition of vasculogenesis and angiogenesis by other receptor-mediated pathways, including the pathway comprising the flt-I receptor.

Receptor tyrosine kinase mediated signal transduction is initiated by extracellular interaction with a specific growth factor (ligand), followed by receptor dimerization, transient stimulation of the intrinsic protein tyrosine kinase activity and autophosphorylation. Binding sites are thereby created for intracellular signal transduction molecules which leads to the formation of complexes with a spectrum of cytoplasmic signalling molecules that facilitate the appropriate cellular response, e.g., cell division and metabolic effects to the extracellular microenvironment. See, Schlessinger and Ullrich, 1992, *Neuron*, 9:1–20.

The close homology of the intracellular regions of KDR/FLK-1 with that of the PDGF-β receptor (50.3% homology) and/or the related flt-I receptor indicates the induction of overlapping signal transduction pathways. For example, for the PDGF-β receptor, members of the src family (Twamley et al., 1993, *Proc. Natl. Acad. Sci. USA*, 90:7696–7700), phosphatidylinositol-3'-kinase (Hu et al., 1992, *Mol. Cell. Biol.*, 12:981–990), phospholipase cy (Kashishian & Cooper, 1993, *Mol. Cell. Biol.*, 4:49–51), ras-GTPase-activating protein, (Kashishian et al., 1992, *EMBO J.*, 11:1373–1382), PTP-ID/syp (Kazlauskas et al., 1993, *Proc. Natl. Acad. Sci. USA*, 10 90:6939–6943), Grb2 (Arvidsson et al., 1994, *Mol. Cell. Biol.*, 14:6715–6726), and the adapter molecules Shc and Nck (Nishimura et al., 1993, *Mol. Cell. Biol.*, 13:6889–6896), have been shown to bind to regions involving different autophosphorylation sites. See generally, Claesson-Welsh, 1994, *Prog. Growth Factor Res.*, 5:37–54. Thus, it is likely that signal transduction pathways activated by KDR/FLK-1 include the ras pathway (Rozakis et al., 1992, *Nature*, 360:689–692), the PI-3'-kinase, the src-mediated and the plcy-mediated pathways. Each of these pathways may play a critical role in the angiogenic and/or vasculogenic effect of KDR/FLK-1 in endothelial cells. Consequently, a still further aspect of this invention relates to the use of the organic compounds described herein to modulate angiogenesis and vasculogenesis as such processes are controlled by these pathways.

Conversely, disorders related to the shrinkage, contraction or closing of blood vessels, such as restenosis, are also implicated and may be treated or prevented by the methods of this invention.

Fibrotic disorders refer to the abnormal formation of extracellular matrices. Examples of fibrotic disorders include hepatic cirrhosis, mesangial cell proliferative disorders and pulmonary fibrosis. Hepatic cirrhosis is characterized by the increase in extracellular matrix constituents resulting in the formation of a hepatic scar. An increased extracellular matrix resulting in a hepatic scar can also be caused by a viral infection such as hepatitis. Lipocytes appear to play a major role in hepatic cirrhosis. Other fibrotic disorders implicated include atherosclerosis. Pulmonary fibrosis may result from radiation treatment or treatment with chemotherapeutic drugs.

Mesangial cell proliferative disorders refer to disorders brought about by abnormal proliferation of mesangial cells. Mesangial proliferative disorders include various human renal diseases such as glomerulonephritis, diabetic nephropathy and malignant nephrosclerosis as well as such disorders as thrombotic microangiopathy syndromes, transplant rejection, and glomerulopathies. The RTK PDGFR has been implicated in the maintenance of mesangial cell proliferation. Floege et al., 1993, *Kidney International* 43:47S–54S.

Many cancers are cell proliferative disorders and, as noted previously, PKs have been associated with cell proliferative disorders. Thus, it is not surprising that PKs such as, for example, members of the RTK family have been associated with the development of cancer. Some of these receptors, like EGFR (Tuzi et al., 1991, *Br. J. Cancer* 63:227–233, Torp et al., 1992, *APMIS* 100:713–719) HER2/neu (Slamon et al., 1989, *Science* 244:707–712) and PDGF-R (Kumabe et al., 1992, *Oncogene*, 7:627–633) are over-expressed in many tumors and/or persistently activated by autocrine loops. In fact, in the most common and severe cancers these receptor over-expressions (Akbasak and Suner-Akbasak et al., 1992, *J. Neurol. Sci.*, 111 :119–133, Dickson et al., 1992, *Cancer Treatment Res.* 61:249–273, Korc et al., 1992, *J. Clin. Invest.* 90:1352–1360) and autocrine loops (Lee and Donoghue, 1992, *J. Cell. Biol.*, 118:1057–1070, Korc et al., suPra, Akbasak and Suner-Akbasak et al., supra) have been demonstrated. For example, EGFR has been associated with squamous cell carcinoma, astrocytoma, glioblastoma, head and neck cancer, lung cancer and bladder cancer. HER2 has been associated with breast, ovarian, gastric, lung, pancreas and bladder cancer. PDGFR has been associated with glioblastoma and melanoma as well as lung, ovarian and prostate cancer. The RTK c-met has also been associated with malignant tumor formation. For example, c-met has been associated with, among other cancers, colorectal, thyroid, pancreatic, gastric and hepatocellular carcinomas and lymphomas. Additionally c-met has been linked to leukemia. Over-expression of the c-met gene has also been detected in patients with Hodgkins disease and Burkitts disease.

IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., 1989, *J. Clin. Invest.* 84:1418–1423) and small lung tumor cells (Macauley et al., 1990, *Cancer Res.*, 50:2511–2517). In addition, IGF-I, while integrally involved in the normal growth and differentiation of the nervous system, also appears to be an autocrine stimulator of human gliomas. Sandberg-Nordqvist et al., 1993, *Cancer Res.* 53:2475–2478. The importance of IGF-IR and its ligands in cell proliferation is further supported by the fact that many cell types in culture (fibroblasts, epithelial cells, smooth muscle cells, T-lymphocytes, myeloid cells, chondrocytes and osteoblasts (the stem cells of the bone marrow)) are stimulated to grow by IGF-I. Goldring and Goldring, 1991, *Eukaryotic Gene Expression*, 1:301–326. Baserga and Coppola suggest that IGF-IR plays a central role in the mechanism of transformation and, as such, could be a preferred target for therapeutic interventions for a broad spectrum of human malignancies. Baserga, 1995, *Cancer Res.*, 55:249–252, Baserga, 1994, Cell 79:927–930, Coppola et al., 1994, *Mol. Cell. Biol.*, 14:4588–4595.

STKs have been implicated in many types of cancer including, notably, breast cancer (Cance, et al., *Int. J. Cancer*, 54:571–77 (1993)).

The association between abnormal PK activity and disease is not restricted to cancer. For example, RTKs have been associated with diseases such as psoriasis, diabetes mellitus, endometriosis, angiogenesis, atheromatous plaque development, Alzheimer's disease, restenosis, von Hippel-Lindau disease, epidermal hyperproliferation, neurodegenerative diseases, age-related macular degeneration and hemangiomas. For example, EGFR has been indicated in corneal and dermal wound healing. Defects in Insulin-R and IGF-1R are indicated in type-II diabetes mellitus. A more complete correlation between specific RTKs and their therapeutic indications is set forth in Plowman et al., 1994, *DN&P* 7:334–339.

As noted previously, not only RTKs but CTKs including, but not limited to, src, abl, fps, yes, fyn, lyn, Ick, blk, hck, fgr and yrk (reviewed by Bolen et al., 1992, *FASEB J.*, 6:3403–3409) are involved in the proliferative and metabolic signal transduction pathway and thus could be expected, and have been shown, to be involved in many PTK-mediated disorders to which the present invention is directed. For example, mutated src (v-src) has been shown to be an oncoprotein ($pp60^{v-src}$) in chicken. Moreover, its cellular homolog, the proto-oncogene $pp60^{c-src}$ transmits oncogenic signals of many receptors. Over-expression of EGFR or HER2/neu in tumors leads to the constitutive activation of $pp60^{c-src}$ which is characteristic of malignant cells but absent in normal cells. On the other hand, mice deficient in the expression of c-src exhibit an osteopetrotic phenotype, indicating a key participation of c-src in osteoclast function and a possible involvement in related disorders.

Similarly, Zap70 has been implicated in T-cell signaling which may relate to autoimmune disorders.

STKs have been associated with inflammation, autoimmune disease, immunoresponses, and hyperproliferation disorders such as restenosis, fibrosis, psoriasis, osteoarthritis and rheumatoid arthritis.

PKs have also been implicated in embryo implantation. Thus, the compounds of this invention may provide an effective method of preventing such embryo implantation and thereby be useful as birth control agents. Additional disorders which may be treated or prevented using the compounds of this invention are immunological disorders such as autoimmune disease, AIDS and cardiovasular disorders such as atherosclerosis.

Finally, both RTKs and CTKs are currently suspected as being involved in hyperimmune disorders.

The compounds and data presented are not to be construed as limiting the scope of this invention in any manner whatsoever.

Pharmaceutical Compositions and Use

A compound of the present invention or a physiologically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

Routes of Administration

Suitable routes of administration may include, without limitation, oral, intraoral, rectal, transmucosal or intestinal administration or intramuscular, epicutaneous, parenteral, subcutaneous, transdermal, intramedullary, intrathecal, direct intraventricular, intravenous, intravitreal, intraperitoneal, intranasal, intramuscular, intradural, intrarespiratory, nasal inhalation or intraocular injections. The preferred routes of administration are oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Composition/Formulation

Pharmaceutical compositions of the present invention may be manufactured by processes well known in the art, e.g., by means of conventional mixing, dissolving, granulating, dragee-making, levigating, emulsifying, encapsulating, entrapping, lyophilizing processes or spray drying.

Pharmaceutical compositions for use in the methods of the present invention may be prepared by any methods of pharmacy, but all methods include the step of bringing in association the active ingredient with the carrier which constitutes one or more necessary ingredients. In particular, pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

Dosage forms include tablets, troches, dispersions, suspensions, solutions, capsules, patches, syrups, elixirs, gels, powders, magmas, lozenges, ointments, creams, pastes, plasters, lotions, discs, suppositories, nasal or oral sprays, aerosols and the like.

For injection, the compounds of the invention may be formulated in aqueous solutions, preferably in physiologically compatible buffers such buffers with or without a low concentration of surfactant or cosolvent, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium m or long chain mono- di- or triglycerides. Stabilizers may be added in these formulations, also.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, maleate, succinate, malate, acetate and methylsulfonate ($CH_3SO_3$), wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide ($Ca(OH)_2$), etc.).

Dosage

Pharmaceutical compositions suitable for use in the present invention include compositions wherein the active ingredients are contained in an amount sufficient to achieve the intended purpose, i.e., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of c-Met activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50–90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%. At present, the therapeutically effective amounts of compounds of Formula (I) may range from approximately 10 mg/m$^2$ to 1000 mg/m$^2$ perday. Even more preferably 25 mg/m$^2$ to 500 mg/m$^2$.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

The following examples are given to illustrate the present invention. It should be understood, however, that the invention is not to be limited to the specific conditions or details described in these examples. Throughout the specification, any and all references to a publicly available documents are specifically incorporated into this patent application by reference.

EXAMPLES

General Synthetic Scheme

General scheme

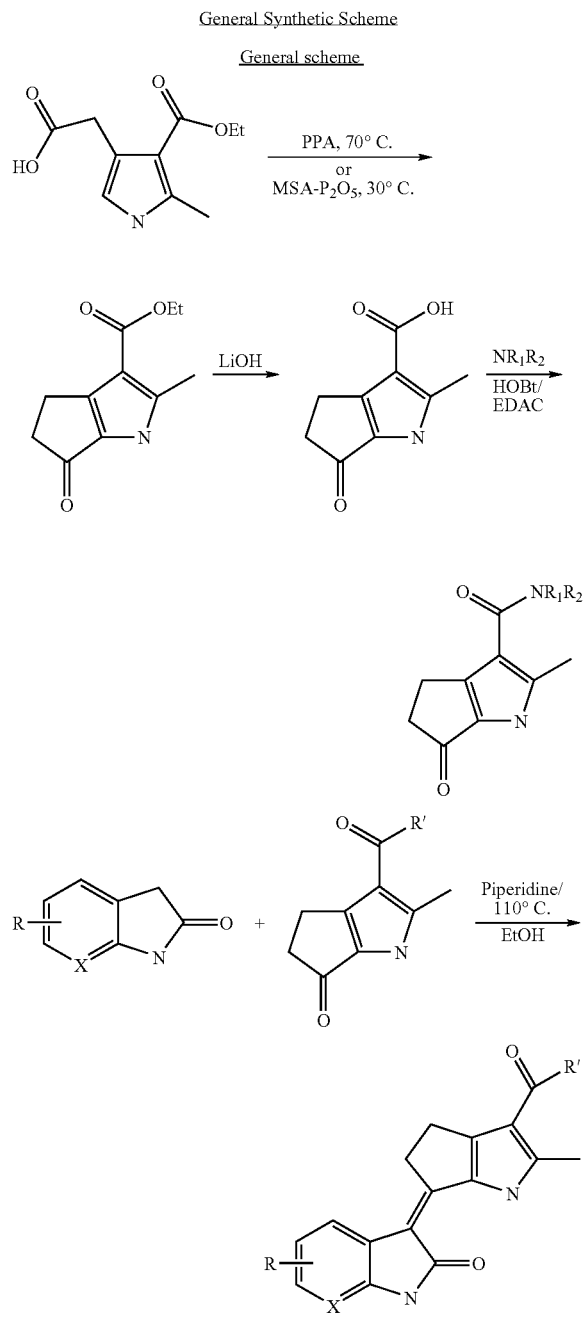

Intermediates

Example A

2-Methyl-6-oxo-1,4,5,6-tetrahydro-cyclopenta[b]pyrrole-3-carboxylic acid ethyl ester

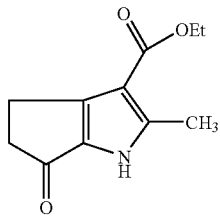

Method 1

Polyphosphoric acid (20 g) and $P_2O_5$ (1.0 g) were mixed together and heated at 70° C. for 20 min. To the mixture was added 3-(4-ethoxycarbonyl-5-methyl-3-pyrrolyl)propanoic acid (1.0 g, 4.44 mmol) and heating was continued for 20 hours. The reaction was poured into ice-water, extracted with EtOAc. The organic layer was washed with brine and sat. $NaHCO_3$, and dried ($MgSO_4$). After removal of the solvent, the crude product was recrystallized from $CH_2Cl_2$-hexane to give (0.78 g, 85%) of 2-methyl-6-oxo-1,4,5,6-tetrahydro-cyclopenta[b]pyrrole-3-carboxylic acid ethyl ester as a white solid.

Method 2

A mixture of methanesulfonic acid (170.0 g) and $P_2O_5$ (17.0 g) was stirred at room temperature to 100° C. for 1 hour until it became a clear solution. The solution was cooled down to 30° C. and then 3-(4-ethoxycarbonyl-5-methyl-3-pyrrolyl)propanoic acid (10.0 g, 44.4 mmol) was added in portions with stirring. The mixture was stirred at 30–40° C. for 4 hours and then was allowed to stay at rt overnight. The reaction was poured into ice-$NaHCO_3$ (60.0 g) slowly. The precipitate was collected by filtration, washed with water, sat. $NaHCO_3$ and water in turn to give 8.95 g (97%) of the titled compound as a gray white solid.

$^1$HNMR (400 MHz, $CDCl_3$) δ 10.8 (br s, 1H, NH), 4.29 (q, J=7 Hz, 2H), 3.03 (m, 2H), 2.88 (m, 2H), 2.68 (s, 3H, $CH_3$), 1.36 (t, J=7 Hz, 3H).

MS m/z 206 [M−1].

Example B

2-Methyl-6-oxo-1,4,5,6-tetrahydro-cyclopenta[b]pyrrole-3-carboxylic acid

A suspension of 2-methyl-6-oxo-1,4,5,6-tetrahydro-cyclopenta[b]pyrrole-3-carboxylic acid

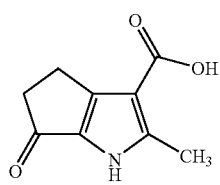

ethyl ester (Example A, 8.28 g, 40 mmol) in 1 N aq. LiOH (150 mL) was stirred at 50–60° C. for 48 hours. A clear yellowish solution was obtained. The reaction was cooled, poured onto ice and acidified with 6 N HCl to pH 3.0. The solid was collected by filtration, washed with water and dried to give 6.55 g (91%) of the titled compound as a white solid.

¹HNMR (400 MHz, DMSO-d$_6$) δ 12.12 (br s, 1H, NH), 12.0 (br s, 1H, COOH), 2.83 (m, 2H), 2.66 (m, 2H), 2.44 (s, 3H, CH$_3$).

MS m/z 178 [M−1].

Example C

2-Methyl-6-oxo-1,4,5,6-tetrahydro-cyclopenta[b] pyrrole-3-carboxylic acid benzylamide

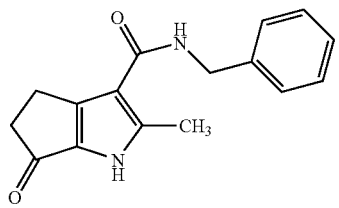

A mixture of 2-methyl-6-oxo-1,4,5,6-tetrahydro-cyclopenta[b]pyrrole-3-carboxylic acid (Example B, 268.5 mg, 1.5 mmol), HOBt (202.5 mg, 1.5 mmol) and EDC (573.5 mg, 3 mmol) in dry DMF (5 mL) was stirred at room temperature for 20 min. Then aniline (3.0 mmol) was added to the mixture and stirring was continued for 24 hours. The reaction was diluted with sat. Na$_2$CO$_3$ and water, the solid was collected by vacuum filtration, washed with sat. Na$_2$CO$_3$ and water in turn, dried to give 315 mg of the titled compound as a white solid.

¹HNMR (400 MHz, DMSO-d$_6$) δ 11.96 (s, 1H, NH), 7.63 (t, 1H), 7.27–7.33 (m, 4H), 7.18–7.23 (m, 1H), 4.4 (d, J=6 Hz, 2H, NCH$_3$), 2.96 (m, 2H), 2.69 (m, 2H), 2.43 (s, 3H, CH$_3$).

MS m/z 267 [M−1].

Example D

2-Methyl-6-oxo-1,4,5,6-tetrahydro-cyclopenta[b] pyrrole-3-carboxylic acid 4-chloro-benzylamide

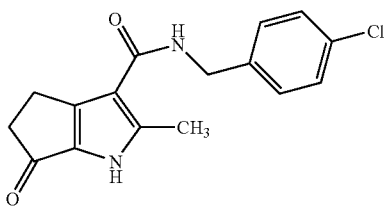

Procedure as Example C, but 4-chloroaniline was used to give 403 mg of the titled compound as a white solid.

¹HNMR (400 MHz, DMSO-d$_6$) δ 11.98 (s, 1H, NH), 7.65 (t, 1H), 7.29–7.37 (m, 4H), 4.38 (d, J=6 Hz, 2H, NCH$_2$), 2.96 (m, 2H), 2.69 (m, 2H), 2.42 (s, 3H, CH$_3$).

MS m/z 301 [M−1].

Example E

2-Methyl-6-oxo-1,4,5,6-tetrahydro-cyclopenta[b] pyrrole-3-carboxylic acid 2,6-difluoro-benzylamide

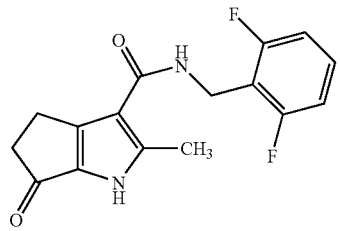

Procedure as Example C, but 2,6-difluoroaniline was used to give 401 mg of the titled compound as a white solid.

¹HNMR (400 MHz, DMSO-d$_6$) δ 11.93 (s, 1H, NH), 7.52 (t, 1H), 7.37 (m, 1H), 7.05 (m, 2H), 4.45 (d, J=6 Hz, 2H, NCH$_2$), 2.87 (m, 2H), 2.66 (m, 2H), 2.38 (s, 3H, CH$_3$).

MS m/z 303 [M−1].

Example F

2-Methyl-3-((S)-2-pyrrolidin-1-ylmethyl-pyrrolidine-1-carbonyl)-4,5-dihydro-1H-cyclopenta[b]pyrrol-6-one

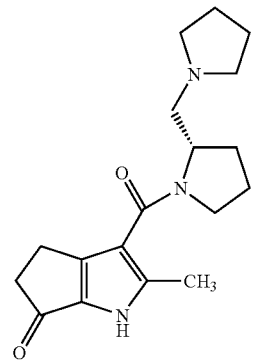

A mixture of 2-methyl-6-oxo-1,4,5,6-tetrahydro-cyclopenta[b]pyrrole-3-carboxylic acid (Example B, 3.58 g, 20 mmol), HOBt (2.7 g, 20 mmol) and EDC (5.74 g, 30 mmol) in dry DMF (50 mL) was stirred at 0° C. to room temperature for 20 min. Then (S)-(+)-1-(2-pyrrolidinylmethyl)pyrrolidine (24 mmol) was added and stirring was continued for 48 hours. The solvent was removed under reduced pressure and the residue was dissolved in EtOAc, washed with sat. Na$_2$CO$_3$, dried, concentrated and purified on a silica gel column to give 5.1 g (81%) of the titled compound as a yellowish foam.

¹HNMR (400 MHz, DMSO-d$_6$) δ 11.85 (s, 1H, NH), 4.2 (br m, 1H), 3.38 (m, 2H), 2.75 (m, 1H), 2.66 (m, 2H), 2.65 (m, 1H), 2.4 (m, 6H), 2.24 (s, 3H, CH$_3$), 1.96 (m, 1H), 1.81 (m, 3H), 1.6 (m, 4H).

MS m/z 314 [M−1].

Example 1

2-Methyl-6-[2-oxo-1,2-dihydro-indol-(3Z)-ylidene]-1,4,5,6-tetrahydro-cyclopenta[b]pyrrole-3-carboxylic acid ethyl ester

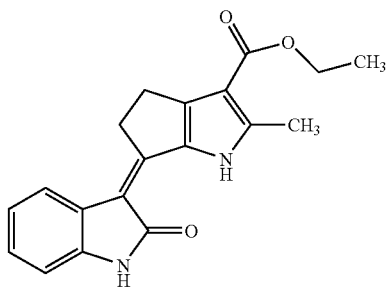

A mixture of oxindole (44 mg, 0.33 mmol) and 2-methyl-6-oxo-1,4,5,6-tetrahydro-cyclopenta[b]pyrrole-3-carboxylic acid ethyl ester (Example A, 62 mg, 0.3 mmol) in DMF (5 mL)-piperidine (0.5 mL) was heated at 110° C. with stirring for 72 hours. Most of the solvent was removed under reduced pressure and the residue was diluted with ethanol. The resulted precipitate was collected by filtration, washed with ethanol and dried to give 56 mg (58%) of the titled compound as a yellow solid.

$^1$HNMR (400 MHz, CDCl$_3$) δ 11.61 (brs, 1H, NH), 7.6 (s, 1H, NH), 7.44 (d, 1H), 7.15 (t, 1H), 7.07 (t, 1H), 6.91 (d, 1H), 4.3 (q, J=7 Hz, 2H), 3.57 (m, 2H), 3.17 (m, 2H), 2.66 (s, 3H, CH$_3$), 1.37 (t, J=7 Hz, 3H).

MS m/z 321 [M−1].

Example 2

6-[5-(2,6-Dichloro-phenylmethanesulfonyl)-2-oxo-1,2-dihydro-indol-(3Z)-ylidene]-2-methyl-1,4,5,6-tetrahydro-cyclopenta[b]pyrrole-3-carboxylic acid ethyl ester

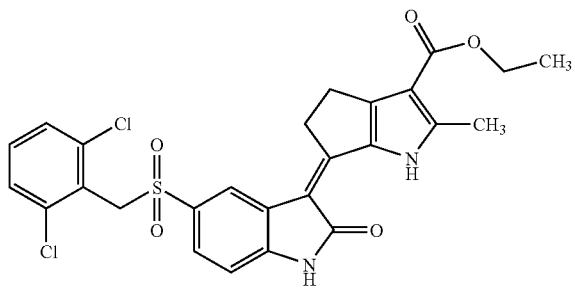

Similar procedure as Example 1 to give 48% of the titled compound as a yellow solid.

$^1$HNMR (400 MHz, DMSO-d$_6$) δ 11.67 (s, 1H, NH), 11.14 (s, 1H, NH), 7.49 (m, 4H), 7.39 (dd, 1H), 7.03 (d, 1H), 4.85 (s, 2H), 4.2 (q, J=7 Hz, 2H), 3.34 (m, 2H), 3.04 (m, 2H), 2.63 (s, 3H, CH$_3$), 1.28 (t, J=7 Hz, 3H).

MS m/z 543 [M−1].

Example 3

2-Methyl-6-[5-methylsulfamoyl-2-oxo-1,2-dihydro-indol-(3Z)-ylidene]-1,4,5,6-tetrahydro-cyclopenta[b]pyrrole-3-carboxylic acid ethyl ester

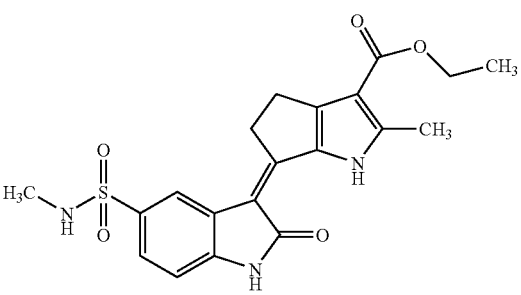

Similar procedure as Example 1 to give 63% of the titled compound as a yellow solid.

$^1$HNMR (400 MHz, DMSO-d$_6$) δ 11.69 (s, 1H, NH), 11.01 (s, 1H, NH), 7.75 (d, 1H), 7.53 (dd, J=2 & 8 Hz, 1H), 7.3 (q, 1H, NH), 7.0 (d, J=8 Hz, 1H), 4.18 (q, J=7 Hz, 2H), 3.56 (m, 2H), 3.07 (m, 2H), 2.61 (s, 3H, CH$_3$), 2.37 (d, J=5 Hz, 3H, NCH$_3$), 1.27 (t, J=7 Hz, 3H).

MS m/z 414 [M−1].

Example 4

3-[2-Methyl-4,5-dihydro-1H-cyclopenta[b]pyrrol-(6Z)-ylidene]-2-oxo-2,3-

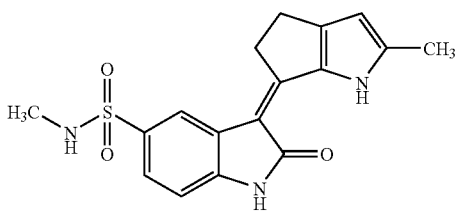

dihydro-1H-indole-5-sulfonic acid methylamide

See Example 5.

$^1$HNMR (400 MHz, DMSO-d$_6$) δ 11.36 (s, 1H, NH), 10.91 (s, 1H, NH), 7.74 (d, 1H), 7.48 (dd, 1H), 7.25 (q, 1H, NH), 6.99 (d, 1H), 6.02 (s, 1H), 3.56 (m, 2H), 2.93 (m, 2H), 2.39 (s, 3H, CH$_3$), 2.37 (d, J=5 Hz, 3H, NCH$_3$).

MS m/z 342 [M−1].

Example 5

2-Methyl-6-[5-methylsulfamoyl-2-oxo-1,2-dihydro-indol-(3Z)-ylidene]-1,4,5,6-tetrahydro-cyclopenta[b]pyrrole-3-carboxylic acid

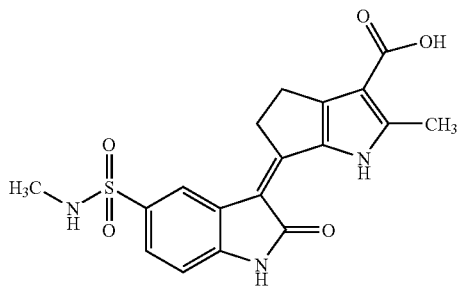

A mixture of 2-oxo-2,3-dihydro-1H-indole-5-sulfonic acid methylamide (905 mg, 4 mmol) and 2-methyl-6-oxo-1,4,5,6-tetrahydro-cyclopenta[b]pyrrole-3-carboxylic acid (Example B, 716 mg, 4 mmol) in DMF (50 mL) and piperidine (5 mL) was heated at 110° C. with stirring for 48 hours. The solvent was removed and the residue was suspended in methanol-ice-water and acidified with 2N HCl. The solid was collected by filtration and then suspended in DCM. The suspension was washed with 2N aq. NaOH for three times. The combined water layer was backwashed with DCM. The water layer was acidified with 2N HCl and filtered to give a brown solid, which was triturated with MeOH to afford 380 mg of the titled compound as a brown yellow solid. The combined organic layer was dried (Na$_2$SO$_4$) and evaporated to give 130 mg of 3-[2-methyl-4,5-dihydro-1H-cyclopenta[b]pyrrol-(6Z)-ylidene]-2-oxo-2,3-dihydro-1H-indole-5-sulfonic acid methylamide (Example 4) as a yellow solid.

$^1$HNMR (400 MHz, DMSO-d$_6$) δ 12.16 (brs, 1H, COOH), 11.64 (s, 1H, NH), 11.0 (s, 1H, NH), 7.75 (d, 1H), 7.52 (dd, J=2 & 8 Hz, 1H), 7.3 (q, 1H, NH), 7.0 (d, J=8 Hz, 1H), 3.56 (m, 2H), 3.07 (m, 2H), 2.61 (s, 3H, CH$_3$), 2.36 (d, J=5 Hz, 3H, NCH$_3$).

MS m/z 386 [M−1].

Example 6

6-[5-Methanesulfonyl-2-oxo-1,2-dihydro-indol-(3Z)-ylidene]-2-methyl-1,4,5,6-tetrahydro-cyclopenta[b]pyrrole-3-carboxylic acid ethyl ester

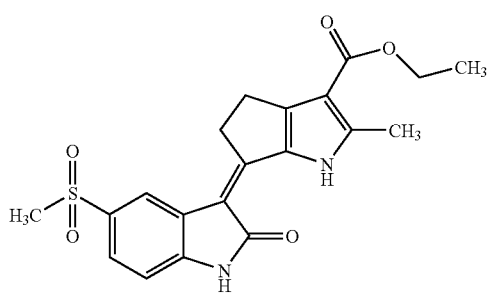

Similar procedure as Example 1 to give 65% of the titled compound as a yellow solid.

$^1$HNMR (400 MHz, DMSO-d$_6$) δ 11.69 (s, 1H, NH), 11.09 (s, 1H, NH), 7.82 (s, 1H), 7.66 (d, 1H), 7.05 (d, 1H), 4.19 (q, J=7 Hz, 2H), 3.64 (m, 2H), 3.18 (s, 3H, CH$_3$), 3.08 (m, 2H), 2.62 (s, 3H, CH$_3$), 1.27 (t, J=7 Hz, 3H).

MS m/z 399 [M−1].

Example 7

6-[5-Dimethylsulfamoyl-2-oxo-1,2-dihydro-indol-(3Z)-ylidene]-2-methyl-1,4,5,6-tetrahydro-cyclopenta[b]pyrrole-3-carboxylic acid ethyl ester

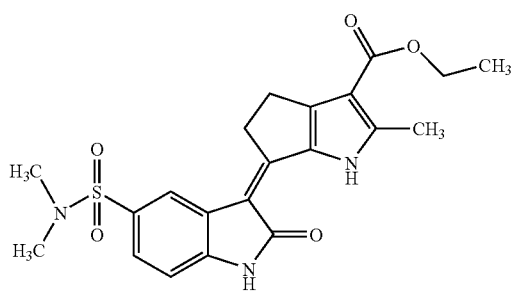

Similar procedure as Example 1 to give 59% of the titled compound as a yellow solid.

$^1$HNMR (400 MHz, DMSO-d$_6$) δ 11.68 (s, 1H, NH), 11.07 (s, 1H, NH), 7.62 (d, 1H), 7.49 (dd, J=2 & 8 Hz, 1H), 7.06 (d, J=8 Hz, 1H), 4.18 (q, J=7 Hz, 2H), 3.57 (m, 2H), 3.05 (m, 2H), 2.61 (s, 3H, CH$_3$), 2.59 (s, 6H, N(CH$_3$)$_2$), 1.26 (t, J=7 Hz, 3H).

MS m/z 428 [M−1].

Example 8

6-[5-Isopropylsulfamoyl-2-oxo-1,2-dihydro-indol-(3Z)-ylidene]-2-methyl-1,4,5,6-tetrahydro-cyclopenta[b] pyrrole-3-carboxylic acid ethyl ester

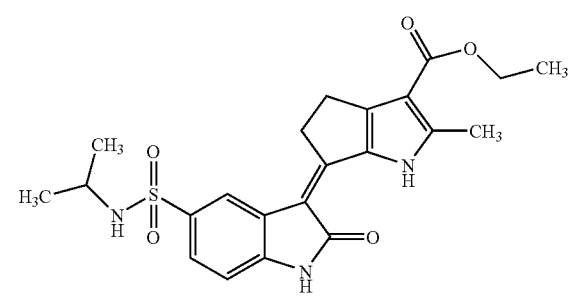

Similar procedure as Example 1 to give 65% of the titled compound as a yellow solid.

$^1$HNMR (400 MHz, DMSO-d$_6$) δ 11.68 (s, 1H, NH), 10.99 (s, 1H, NH), 7.79 (d, 1H), 7.55 (dd, J=2 & 8 Hz, 1H), 7.43 (d, J=7 Hz, 1H, NH), 6.98 (d, J=8 Hz, 1H), 4.18 (q, J=7 Hz, 2H), 3.55 (m, 2H), 3.18 (m, 1H), 3.07 (m, 2H), 2.61 (s, 3H, CH$_3$), 1.26 (s, 3H, CH$_3$), 0.93 (d, J=6 Hz, 6H, 2×CH$_3$).

MS m/z 442 [M−1].

Example 9

6-[5-Ethanesulfonyl-2-oxo-1,2-dihydro-indol-(3Z)-ylidene]-2-methyl-1,4,5,6-tetrahydro-cyclopenta[b]pyrrole-3-carboxylic acid ethyl ester

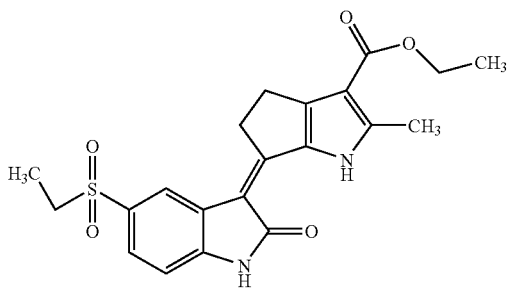

Similar procedure as Example 1 to give 40% of the titled compound as a yellow solid.

$^1$HNMR (400 MHz, DMSO-$d_6$) δ 11.68 (s, 1H, NH), 11.1 (s, 1H, NH), 7.76 (d, 1H), 7.6 (dd, J=2 & 8 Hz, 1H), 7.05 (d, J=8 Hz, 1H), 4.18 (q, J=7 Hz, 2H), 3.76 (m, 2H), 3.25 (q, J=7 Hz, 2H), 3.06 (m, 2H), 2.61 (s, 3H, CH$_3$), 1.27 (t, J=7 Hz, 3H), 1.10 (t, J=7 Hz, 3H)).

MS m/z 413 [M−1].

Example 10

2-Methyl-6-[5-methylsulfamoyl-2-oxo-1,2-dihydro-indol-(3Z)-ylidene]-1,4,5,6-tetrahydro-cyclopenta[b]pyrrole-3-carboxylic acid (2-hydroxy-3-pyrrolidin-1-yl-propyl)-amide

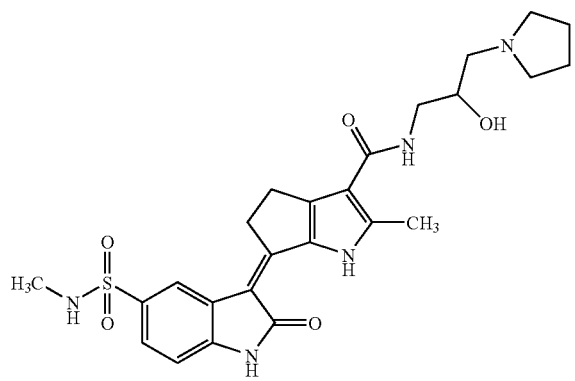

A mixture of 2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid (Example 5, 78 mg, 0.2 mmol), HOBt (27 mg, 0.2 mmol) and EDC (77 mg, 0.4 mmol) in dry DMF (2 mL) was stirred at room temperature for 30 min. Then 1-amino-3-pyrrolidine-1-yl-propan-2-ol (0.4 mmol) was added and stirring was continued for 48 hours. The solvent was removed under reduced pressure and the residue was crystallized and purified on a silica gel column to give 54 mg of the titled compound as a yellow solid.

$^1$HNMR (400 MHz, DMSO-$d_6$) δ 11.6 (s, 1H, NH), 11.0 (s, 1H, NH), 7.76 (d, 1H), 7.52 (dd, J=2 & 8 Hz, 1H), 7.28 (q, 1H, NH), 7.11 (t, 1H, NH), 7.01 (d, J=8 Hz, 1H), 4.85 (m, 1H, OH), 3.71 (m, 1H), 3.61 (m, 2H), 3.18 (m, 2H), 3.15 (m, 2H), 3.3–3.4 (m, 2H), 2.59 (s, 3H, CH$_3$), 2.5 (m, 4H), 2.37 (d, J=5 Hz, 3H, NCH$_3$), 1.66 (m, 4H).

MS m/z 512 [M−1].

Example 11

2-Methyl-6-[5-methylsulfamoyl-2-oxo-1,2-dihydro-indol-(3Z)-ylidene]-1,4,5,6-tetrahydro-cyclopenta[b]pyrrole-3-carboxylic acid (3-cyclopropylamino-2-hydroxy-propyl)-amide Procedure as Example 10, but 1-amino-3-cyclopropylamino-propan-2-ol was used to give 53

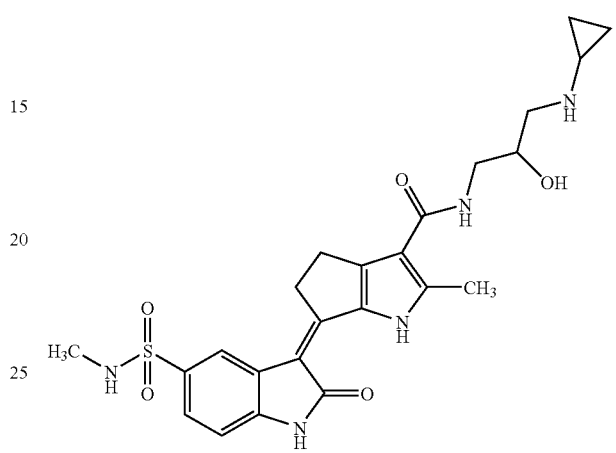

mg of the titled compound as a yellow solid.

$^1$HNMR (400 MHz, DMSO-$d_6$) δ 11.61 (s, 1H, NH), 11.01 (s, 1H, NH), 7.77 (d, 1H), 7.53 (dd, J=2 & 8 Hz, 1H), 7.29 (q, 1H, NH), 7.14 (t, 1H, NH), 7.02 (9d, J=8 Hz, 1H), 4.86 (d, 1H, OH), 3.67 (m, 1H), 3.62 (m, 2H), 3.3 (m, 2H), 3.22 (m, 1H), 3.17 (m, 2H), 2.6 (m, 2H), 2.59 (s, 3H, CH$_3$), 2.38 (d, J=5 Hz, 3H, NCH$_3$), 2.09 (m, 1H), 0.35 (m, 2H), 0.22 (m, 2H).

MS m/z 500 [M+1].

Example 12

2-Methyl-6-[5-methylsulfamoyl-2-oxo-1,2-dihydro-indol-(3Z)-ylidene]-1,4,5,6-tetrahydro-cyclopenta[b]pyrrole-3-carboxylic acid (2-dimethylamino-ethyl)-amide

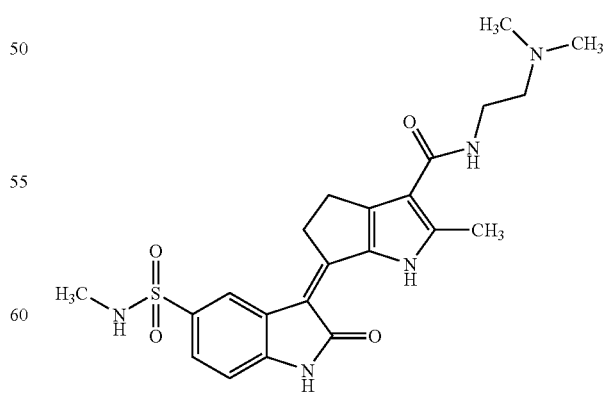

Procedure as Example 10, but N,N-dimethylethylenediamine was used to give 55 mg of the titled compound as an orange solid.

¹HNMR (400 MHz, DMSO-d₆) δ 11.58 (s, 1H, NH), 11.0 (s, 1H, NH), 7.76 (d, 1H), 7.52 (dd, J=2 & 8 Hz, 1H), 7.28 (q, 1H, NH), 7.06 (t, 1H, NH), 7.0 (d, J=8 Hz, 1H), 3.6 (m, 2H), 3.29 (m, 2H), 3.14 (m, 2H), 2.58 (s, 3H, CH₃), 2.38 (t, 2H), 2.37 (d, J=5 Hz, 3H, NCH₃), 2.18 (s, 3H, N(CH₃)₂. MS m/z 456 [M−1].

Example 13

3-[2-Methyl-3-((R)-2-pyrrolidin-1-ylmethyl-pyrrolidine-1-carbonyl)-4,5-dihydro-1H-cyclopenta[b]pyrrol-(6Z)-ylidene]-2-oxo-2,3-dihydro-1H-indole-5-sulfonic acid methylamide

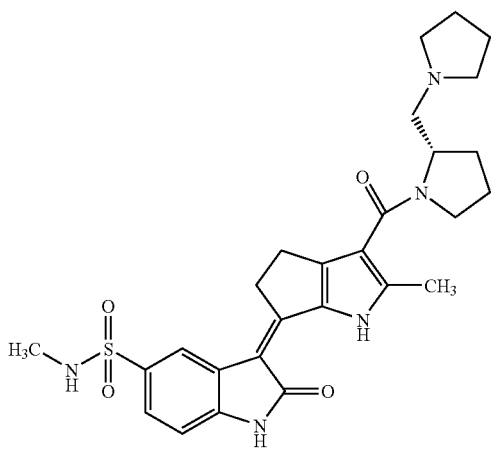

Procedure as Example 10, but (S)-(+)-1-(2-pyrrolidinylmethyl)pyrrolidine was used to give 54 mg of the titled compound as a yellow solid.

¹HNMR (400 MHz, DMSO-d₆) δ 11.56 (brs, 1H, NH), 10.98 (s, 1H, NH), 7.75 (d, 1H), 7.51 (dd, J=2 & 8 Hz, 1H), 7.28 (q, 1H, NH), 7.01 (d, J=8 Hz, 1H), 4.22 (br m, 1H), 3.59 (m, 2H), 3.42 (m, 2H), 2.96 (m, 2H), 2.46 (m, 6H), 2.4 (s, 3H, CH₃), 2.37 (d, J=5 Hz, 3H, NCH₃), 2.0 (m, 1H), 1.84 (m, 3H), 1.62 (m, 4H).

Example 14

2-Methyl-6-[2-oxo-5-sulfamoyl-1,2-dihydro-indol-(3Z)-ylidene]-1,4,5,6-tetrahydro-cyclopenta[b]pyrrole-3-carboxylic acid ethyl ester

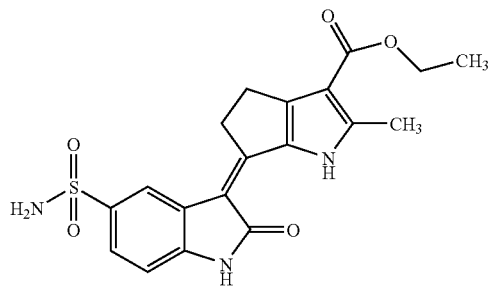

Similar procedure as Example 1 to give 75% of the titled compound as a yellow solid.

¹HNMR (400 MHz, DMSO-d₆) δ 11.70 (s, 1H, NH), 10.97 (s, 1H, NH), 7.85 (s, 1H), 7.58 (d, 1H), 7.2 (s, 2H, NH₂), 6.97 (d, 1H), 4.2 (q, J=7 Hz, 2H), 3.57 (m, 2H), 3.09 (m, 2H), 2.62 (s, 3H, CH₃), 1.27 (t, J=7 Hz, 3H).

MS m/z 400 [M−1].

Example 15

3-Cyclopentylidene-2-oxo-2,3-dihydro-1H-indole-5-sulfonic acid methylamide

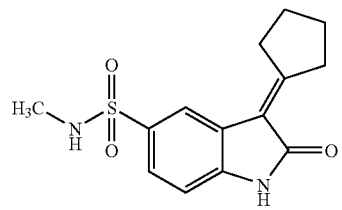

Similar procedure as Example 1 to give 73% of the titled compound as a gray solid.

¹HNMR (400 MHz, DMSO-d₆) δ 10.84 (s, 1H, NH), 7.73 (d, 1H), 7.59 (dd, J=2 & 8 Hz, 1H), 7.31 (q, 1H, NH), 6.98 (d, J=8 Hz, 1H), 2.99 (t, 2H), 2.86 (t, 2H), 2.35 (d, J=5 Hz, 3H, NCH₃), 1.83 (m, 2H), 1.75 (m, 2H).

MS m/z 291 [M−1].

Example 16

3-[3-Methanesulfonyl-2-methyl-4,5-dihydro-1H-cyclopenta[b]pyrrol-(6Z)-ylidene]-2-oxo-2,3-dihydro-1H-indole-5-sulfonic acid methylamide

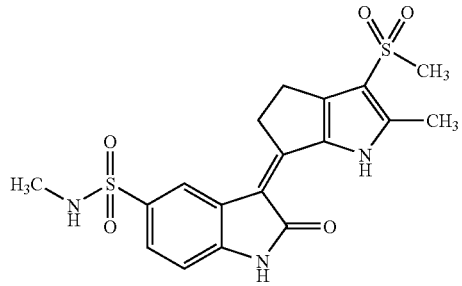

Similar procedure as Example 1 to give 73% of the titled compound as a yellow solid.

¹HNMR (400 MHz, DMSO-d₆) δ 11.82 (s, 1H, NH), 11.06 (s, 1H, NH), 7.76 (d, 1H), 7.55 (dd, J=2 & 8 Hz, 1H), 7.32 (q, 1H, NH), 7.02 (d, J=8 Hz, 1H), 3.59 (m, 2H), 3.13 (s, 3H, CH₃), 3.10 (m, 2H), 2.6 (s, 3H, CH₃), 2.37 (d, J=5 Hz, 3H, NCH₃).

MS m/z 420 [M−1].

Example 17

{6-Methoxy-3-[5-methylsulfamoyl-2-oxo-1,2-dihydro-indol-(3Z)-ylidene]-indan-1-yl}-acetic acid

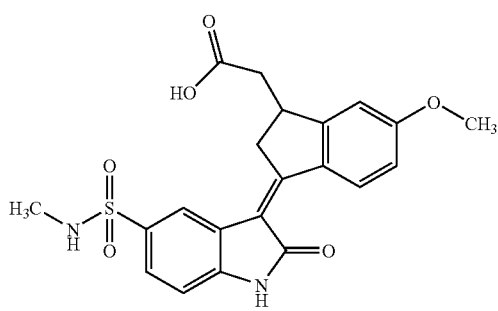

Similar procedure as Example 1 to give 28% of the titled compound as a green yellow solid.

¹HNMR(400 MHz, DMSO-d$_6$) δ 12.35 (s, 1H, COOH), 10.96 (s, 1H, NH), 9.47 (d, J=9 Hz, 1H), 7.86 (s, 1H), 7.6 (d, 1H), 7.29 (q, 1H, NH), 7.12 (d, 1H), 6.99 (d, J=8 Hz, 1H), 6.95 (dd, 1H), 3.84 (s, 3H, OCH$_3$), 3.64–3.76 (m, 2H), 3.3 (d, 1H), 2.92 (dd, 1H), 2.55 (m, 1H), 2.4 (d, J=5 Hz, 3H, NCH$_3$).

MS m/z 427 [M−1].

Example 18

5-Fluoro-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one

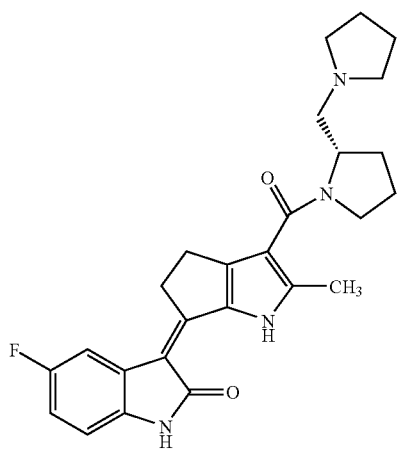

Similar procedure as Example 1 to give 62% of the titled compound as a green yellow solid.

¹HNMR (400 MHz, DMSO-d$_6$) δ 11.62 (s, 1H, NH), 10.57 (s, 1H, NH), 7.2 (dd, 1H), 6.9 (m, 1H), 6.83 (dd, 1H), 4.22 (br m, 1H), 3.56 (m, 2H), 3.42 (m, 2H), 2.92 (m, 2H), 2.48 (m, 6H), 2.41 (s, 3H, CH$_3$), 2.0 (m, 1H), 1.85 (m, 3H), 1.64 (m, 4H).

MS m/z 449 [M+1].

Example 19

6-Methoxy-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one

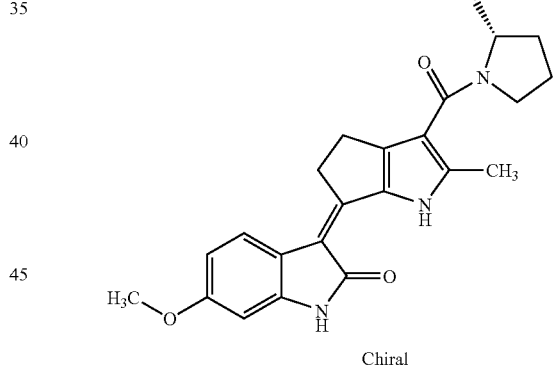

Chiral

Similar procedure as Example 1 to give 70% of the titled compound as a yellow solid.

¹HNMR (400 MHz, DMSO-d$_6$) δ 11.42 (br s, 1H, NH), 10.5 (s, 1H, NH), 7.28 (d, J=8 Hz,1H), 6.53 (dd, J=2 & 8 Hz, 1H), 6.44 (d, J=2 Hz, 1H), 4.2 (br m, 1H), 3.73 (s, 3H, OCH$_3$), 3.46 (m, 2H), 3.41 (m, 2H), 2.9 (m, 2H), 2.48 (m, 6H), 2.36 (s, 3H, CH$_3$), 1.99 (m, 1H), 1.83 (m, 3H), 1.61 (m, 4H).

MS m/z 461 [M−1].

Example 20

4-Methoxy-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one

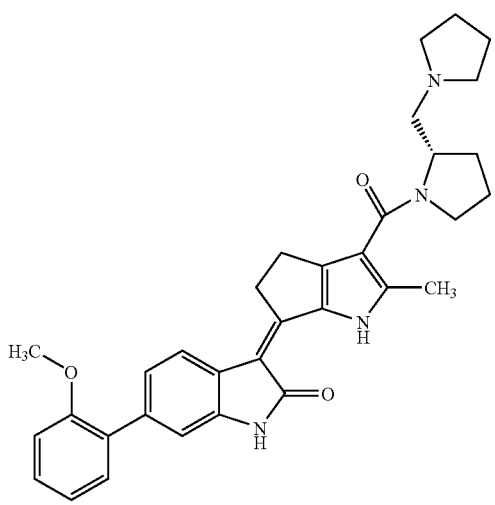

Similar procedure as Example 1 to give 63% of the titled compound as a yellow solid.

$^{1}$HNMR (400 MHz, DMSO-d$_{6}$) δ 11.58 (brs, 1H, NH), 10.55 (s, 1H, NH), 7.41 (d, 1H), 7.29 (m, 2H), 7.0–7.1 (m, 3H), 6.99 (d, 1H), 4.2 (br m, 1H), 3.75 (s, 3H, OCH$_{3}$), 3.55 (m, 2H), 3.42 (m, 2H), 2.92 (m, 2H), 2.45 (m, 6H), 2.39 (s, 3H, CH$_{3}$), 2.0 (m, 1H), 1.84 (m, 3H), 1.62 (m, 4H).

MS m/z 535 [M−1].

Example 21

7-Chloro-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one

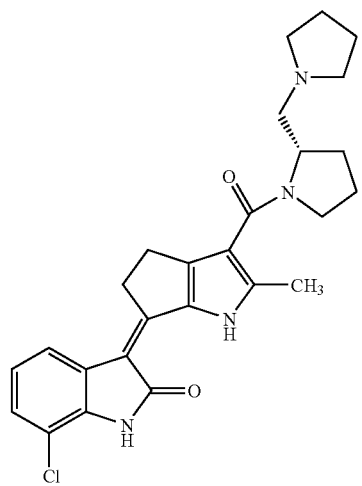

Similar procedure as Example 1 to give 57% of the titled compound as a green yellow solid.

$^{1}$HNMR (400 MHz, DMSO-d$_{6}$) δ 11.58 (brs, 1H, NH), 10.90 (s, 1H, NH), 7.36 (d, J=8 Hz, 1H), 7.12 (dd, 1H), 6.97 (t, 1H), 4.22 (br m, 1H), 3.55 (m, 2H), 3.41 (m, 2H), 2.91 (m, 2H), 2.46 (m, 6H), 2.4 (s, 3H, CH$_{3}$), 1.98 (m, 1H), 1.84 (m, 3H), 1.62 (m, 4H).

MS m/z 463 [M−1].

Example 22

3-[2-Methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-pyrrolo[2,3-b]pyridin-2-one

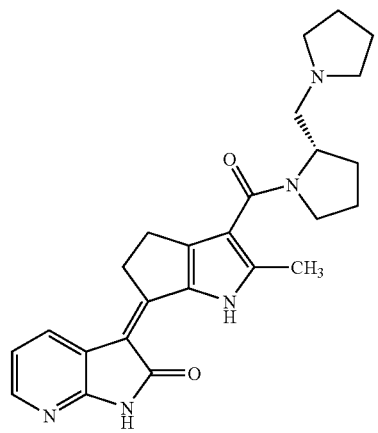

Similar procedure as Example 1 to give 21% of the titled compound as a yellow solid.

$^{1}$HNMR (400 MHz, DMSO-d$_{6}$) δ 11.46 (br s, 1H, NH), 11.08 (s, 1H, NH), 7.95 (dd, 1H), 7.66 (d, 1H), 6.95 (dd, 1H), 4.2 (br m, 1H), 3.54 (m, 2H), 3.41 (m, 2H), 2.92 (m, 2H), 2.45 (m, 6H), 2.4 (s, 3H, CH$_{3}$), 1.98 (m, 1H), 1.84 (m, 3H), 1.61 (m, 4H).

MS m/z 430 [M−1].

Example 23

6-(4-Methoxy-phenyl)-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one

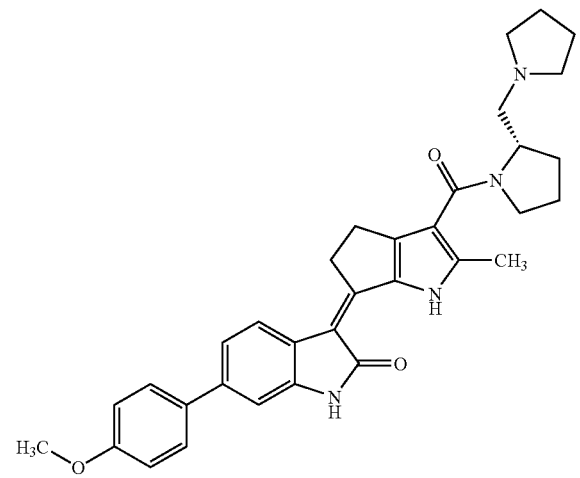

Similar procedure as Example 1 to give 63% of the titled compound as a yellow solid.

$^1$HNMR (400 MHz, DMSO-$d_6$) δ 11.55 (br s, 1H, NH), 10.61 (s, 1H, NH), 7.55 (m, 2H), 7.43 (d, J=8 Hz, 1H), 7.21 (dd, J=2 & 8 Hz, 1H), 7.04 (d, J=2 Hz, 1H), 7.01 (m, 2H), 4.2 (br m, 1H), 3.78 (s, 3H, OCH$_3$), 3.55 (m, 2H), 3.42 (m, 2H), 2.92 (m, 2H), 2.5 (m, 6H), 2.39 (s, 3H, CH$_3$), 2.0 (m, 1H), 1.84 (m, 3H), 1.62 (m, 4H).

MS m/z 535 [M−1].

It will be appreciated that, in any given series of compounds, a range of biological activities will be observed. In its presently preferred aspects, this invention relates to novel geometrically restricted, substituted indolinones capable of modulating, regulating and/or inhibiting protein kinase activity. The following assays may be employed to select those compounds demonstrating the optimal degree of the desired activity.

Assay Procedures

The following in vitro assays may be used to determine the level of activity and effect of the different compounds of the present invention on one or more of the PKs. Similar assays can be designed along the same lines for any PK using techniques well known in the art.

Several of the assays described herein are performed in an ELISA (Enzyme-Linked Immunosorbent Sandwich Assay) format (Voller, et al., 1980, "Enzyme-Linked Immunosorbent Assay," Manual of Clinical Immunology, 2d ed., Rose and Friedman, Am. Soc. Of Microbiology, Washington, D.C., pp. 359–371). The general procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The presently preferred protocols for conducting the ELISA experiments for specific PKs is provided below. However, adaptation of these protocols for determining the activity of compounds against other RTKs, as well as for CTKs and STKs, is well within the scope of knowledge of those skilled in the art.

Other assays described herein measure the amount of DNA made in response to activation of a test kinase, which is a general measure of a proliferative response. The general procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as 5-bromodeoxyuridine (BrdU) or H$^3$-thymidine is added. The amount of labeled DNA is detected with either an anti-BrdU antibody or by measuring radioactivity and is compared to control cells not contacted with a test compound.

GST-FLK-1 Bioassay

This assay analyzes the tyrosine kinase activity of GST-Flk1 on poly(glu-tyr) peptides.

Materials and Reagents:

1. Corning 96-well ELISA plates (Corning Catalog No. 25805-96).
2. poly(glu-tyr) 4:1, lyophilizate (Sigma Catalog No. P0275), 1 mg/ml in sterile PBS.
3. PBS Buffer: for 1 L, mix 0.2 g KH$_2$PO$_4$, 1.15 g Na$_2$HPO$_4$, 0.2 g KCl and 8 g NaCl in approx. 900 ml dH$_2$O. When all reagents have dissolved, adjust the pH to 7.2 with HCl. Bring total volume to 1 L with dH$_2$O.
4. PBST Buffer: to 1 L of PBS Buffer, add 1.0 ml Tween-20.
5. TBB–Blocking Buffer: for 1 L, mix 1.21 g TRIS, 8.77 g NaCl, 1 ml TWEEN-20 in approximately 900 ml dH$_2$O. Adjust pH to 7.2 with HCl. Add 10 g BSA, stir to dissolve. Bring total volume to 1 L with dH$_2$O. Filter to remove particulate matter.
6. 1% BSA in PBS: add 10 g BSA to approx. 990 ml PBS buffer, stir to dissolve. Adjust total volume to 1 L with PBS buffer, filter to remove particulate matter.
7. 50 mM Hepes pH 7.5.
8. GST-Flk1cd purified from sf9 recombinant baculovirus transformation (SUGEN, Inc.).
9. 4% DMSO in dH$_2$O.
10. 10 mM ATP in dH$_2$O.
11. 40 mM MnCl$_2$
12. Kinase Dilution Buffer (KDB): mix 10 ml Hepes (pH 7.5), 1 ml 5M NaCl, 40 µL 100 mM sodium orthovanadate and 0.4 ml of 5% BSA in dH$_2$O with 88.56 ml dH$_2$O.
13. NUNC 96-well V bottom polypropylene plates, Applied Scientific Catalog # AS-72092
14. EDTA: mix 14.12 g ethylenediaminetetraacetic acid (EDTA) with approx. 70 ml dH$_2$O. Add 10 N NaOH until EDTA dissolves. Adjust pH to 8.0. Adjust total volume to 100 ml with dH$_2$O.
15. 1° and 2° Antibody Dilution Buffer: mix 10 ml of 5% BSA in PBS buffer with 89.5 ml TBST.
16. Anti-phosphotyrosine rabbit polyclonal antisera (SUGEN, Inc.)
17. Goat anti-rabbit HRP conjugate.
18. ABST solution: To approx. 900 ml dH$_2$O add 19.21 g citric acid and 35.49 g Na$_2$HPO$_4$. Adjust pH to 4.0 with phosphoric acid. Add 2,2'-Azinobis(3-ethyl-benzthiazoline-6-sulfonic acid (ABTS, Sigma, Cat. No. A-1888, hold for approx. ½ hour, filter.
19. 30% Hydrogen Peroxide.
20. ABST/H$_2$O$_2$: add 3 µl of H$_2$O$_2$ to 15 ml of ABST solution.
21. 0.2 M HCl.

Procedure:

1. Coat Corning 96-well ELISA plates with 2 µg of polyEY in 100 µl PBS/well, hold at room temperature for 2 hours or at 4° C. overnight. Cover plates to prevent evaporation.
2. Remove unbound liquid from wells by inverting plate. Wash once with TBST. Pat the plate on a paper towel to remove excess liquid.
3. Add 100 µl of 1% BSA in PBS to each well. Incubate, with shaking, for 1 hr. at room temperature.
4. Repeat step 2.
5. Soak wells with 50 mM HEPES (pH7.5, 150 µl/well).
6. Dilute test compound with dH$_2$O/4% DMSO to 4 times the desired final assay concentration in 96-well polypropylene plates.
7. Add 25 µl diluted test compound to each well of ELISA plate. In control wells, place 25 µl of dH$_2$O/4% DMSO.

8. Dilute GST-Flk1 0.005 µg (5 ng)/well in KDB.
9. Add 50 µl of diluted enzyme to each well.
10. Add 25 µl 0.5 M EDTA to negative control wells.
11. Add 25 µl of 40 mM $MnCl_2$ with 4×ATP (2 µM) to all wells (100 µl final volume, 0.5 µM ATP final concentration in each well).
12. Incubate, with shaking, for 15 minutes at room temperature.
13. Stop reaction by adding 25 µl of 500 mM EDTA to each well.
14. Wash 3× with TBST and pat plate on paper towel to remove excess liquid.
15. Add 100 µl per well anti-phosphotyrosine antisera, 1:10,000 dilution in antibody dilution buffer. Incubate, with shaking, for 90 min. at room temperature.
16. Wash as in step 14.
17. Add 100 µl/well of goat anti-rabbit HRP conjugate (1:6,000 in antibody dilution buffer). Incubate, with shaking, for 90 minutes are room temperature.
18. Wash as in Step 14.
19. Add 100 µl room temperature $ABST/H_2O_2$ solution to each well.
20. Incubate, with shaking for 15 to 30 minutes at room temperature.
21. If necessary, stop reaction by adding 100 µl of 0.2 M HCl to each well.
22. Read results on Dynatech MR7000 ELISA reader with test filter at 410 nM and reference filter at 630 nM.

PYK2 Bioassay

This assay is used to measure the in vitro kinase activity of HA epitope-tagged full length pyk2 (FL.pyk2-HA) in an ELISA assay.

Materials and Reagents:
1. Corning 96-well ELISA plates.
2. 12CA5 monoclonal anti-HA antibody (SUGEN, Inc.)
3. PBS (Dulbecco's Phosphate-Buffered Saline (Gibco Catalog # 450-1300EB)
4. TBST Buffer: for 1 L, mix 8.766 g NaCl, 6.057 g TRIS and 1 ml of 0.1% Triton X-100 in approx. 900 ml $dH_2O$. Adjust pH to 7.2, bring volume to 1 L.
5. Blocking Buffer: for 1 L, mix 100 g 10% BSA, 12.1 g 100 mM TRIS, 58.44 g 1M NaCl and 10 mL of 1% TWEEN-20.
6. FL.pyk2-HA from sf9 cell lysates (SUGEN, Inc.).
7. 4% DMSO in MilliQue $H_2O$.
8. 10 mM ATP in $dH_2O$.
9. 1M $MnCl_2$.
10. 1M $MgCl_2$.
11. 1M Dithioreitol (DTT).
12. 10× Kinase buffer phosphorylation: mix 5.0 ml 1M Hepes (pH 7.5), 0.2 ml 1M $MnCl_2$, 1.0 ml 1 M $MgCl_2$, 1.0 ml 10% Triton X-100 in 2.8 ml $dH_2O$. Just prior to use, add 0.1 ml 1M DTT.
13. NUNC 96-well V bottom polypropylene plates.
14. 500 mM EDTA in $dH_2O$.
15. Antibody dilution buffer: for 100 mL, 1 mL 5% BSA/PBS and 1 mL 10% Tween-20 in 88 mL TBS.
16. HRP-conjugated anti-Ptyr (PY99, Santa Cruz Biotech Cat. No. SC-7020).
17. ABTS, Moss, Cat. No. ABST-2000.
18. 10% SDS.

Procedure:
1. Coat Corning 96 well ELISA plates with 0.5 µg per well 12CA5 anti-HA antibody in 100 µl PBS. Store overnight at 4° C.
2. Remove unbound HA antibody from wells by inverting plate. Wash plate with $dH_2O$. Pat the plate on a paper towel to remove excess liquid.
3. Add 150 µl Blocking Buffer to each well. Incubate, with shaking, for 30 min at room temperature.
4. Wash plate 4× with TBS-T.
5. Dilute lysate in PBS (1.5 µg lysate/100 µl PBS).
6. Add 100 µl of diluted lysate to each well. Shake at room temperature for 1 hr.
7. Wash as in step 4.
8. Add 50 µl of 2× kinase Buffer to ELISA plate containing captured pyk2-HA.
9. Add 25 µL of 400 µM test compound in 4% DMSO to each well. For control wells use 4% DMSO alone.
10. Add 25 µL of 0.5 M EDTA to negative control wells.
11. Add 25 µl of 20 µM ATP to all wells. Incubate, with shaking, for 10 minutes.
12. Stop reaction by adding 25 µl 500 mM EDTA (pH 8.0) to all wells.
13. Wash as in step 4.
14. Add 100 µL HRP conjugated anti-Ptyr diluted 1:6000 in Antibody Dilution Buffer to each well. Incubate, with shaking, for 1 hr. at room temperature.
15. Wash plate 3× with TBST and 1× with PBS.
16. Add 100 µL of ABST solution to each well.
17. If necessary, stop the development reaction by adding 20 µL 10% SDS to each well.
18. Read plate on ELISA reader with test filter at 410 nM and reference filter at 630 nM.

FGFR1 Bioassay

This assay is used to measure the in vitro kinase activity of FGF1-R in an ELISA assay.

Materials and Reagents:
1. Costar 96-well ELISA plates (Corning Catalog #3369).
2. Poly(Glu-Tyr) (Sigma Catalog # P0275).
3. PBS (Gibco Catalog # 450-1300EB)
4. 50 mM Hepes Buffer Solution.
5. Blocking Buffer (5% BSA/PBS).
6. Purified GST-FGFR1 (SUGEN, Inc.)
7. Kinase Dilution Buffer.
  Mix 500 µl 1M Hepes (GIBCO), 20 µl 5% BSA/PBS, 10 µl 100 mM sodium orthovanadate and 50 µl 5M NaCl.
8. 10 mM ATP
9. ATP/$MnCl_2$ phosphorylation mix: mix 20 µL ATP, 400 µL 1 M $MnCl_2$ and 9.56 ml $dH_2O$.
10. NUNC 96-well V bottom polypropylene plates (Applied Scientific Catalog # AS-72092).
11. 0.5M EDTA.
12. 0.05% TBST
  Add 500 µL TWEEN to 1 liter TBS.
13. Rabbit polyclonal anti-phosphotyrosine serum (SUGEN, Inc.).
14. Goat anti-rabbit IgG peroxidase conjugate (Biosource, Catalog # ALI0404).
15. ABTS Solution.
16. $ABTS/H_2O_2$ solution.

Procedure:
1. Coat Costar 96 well ELISA plates with 1 µg per well Poly(Glu-Tyr) in 100 µl PBS. Store overnight at 4° C.
2. Wash coated plates once with PBS.
3. Add 150 µL of 5% BSA/PBS Blocking Buffer to each well. Incubate, with shaking, for 1 hr at room temperature.
4. Wash plate 2× with PBS, then once with 50 mM Hepes. Pat plates on a paper towel to remove excess liquid and bubbles.

5. Add 25 µL of 0.4 mM test compound in 4% DMSO or 4% DMSO alone (controls) to plate.
6. Dilute purified GST-FGFR1 in Kinase Dilution Buffer (5 ng kinase/50 ul KDB/well).
7. Add 50 µL of diluted kinase to each well.
8. Start kinase reaction by adding 25 µl/well of freshly prepared ATP/Mn++ (0.4 ml 1M $MnCl_2$, 40 µL 10 mM ATP, 9.56 ml $dH_2O$), freshly prepared).
9. Stop reaction with 25 µL of 0.5M EDTA.
10. Wash plate 4× with fresh TBST.
11. Make up Antibody Dilution Buffer: For 50 ml, mix 5 ml of 5% BSA, 250 µl of 5% milk and 50 µl of 100 mM sodium vanadate, bring to final volume with 0.05% TBST.
12. Add 100 µl per well of anti-phosphotyrosine (1:10000 dilution in ADB). Incubate, with shaking for 1 hr. at room temperature.
13. Wash as in step 10.
14. Add 100 µl per well of Biosource Goat anti-rabbit IgG peroxidase conjugate (1:6000 dilution in ADB). Incubate, with shaking for 1 hr. at room temperature.
15. Wash as in step 10 and then with PBS to remove bubbles and excess TWEEN.
16. Add 100 µl of $ABTS/H_2O_2$ solution to each well.
17. Incubate, with shaking, for 10 to 20 minutes. Remove any bubbles.
18. Read assay on Dynatech MR7000 ELISA reader: test filter at 410 nM, reference filter at 630 nM.

PDGFR Bioassay

This assay is used to the in vitro kinase activity of PDGFR in an ELISA assay.

Materials and Reagents:
1. Corning 96-well ELISA plates
2. 28D4C10 monoclonal anti-PDGFR antibody (SUGEN, Inc.).
3. PBS.
4. TBST Buffer.
5. Blocking Buffer (same as for EGFR bioassay).
6. PDGFR-β expressing NIH 3T3 cell lysate (SUGEN, Inc.).
7. TBS Buffer.
8. TBS+10% DMSO.
9. ATP.
10. $MnCl_2$.
11. Kinase buffer phosphorylation mix: for 10 ml, mix 250 µl 1M TRIS, 200 µl 5M NaCl, 100 µl 1M $MnCl_2$ and 50 µl 100 mM Triton X-100 in enough $dH_2O$ to make 10 ml.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. Hydrogen peroxide, 30% solution.
18. $ABTS/H_2O_2$.
19. 0.2 M HCl.

Procedure:
1. Coat Corning 96 well ELISA plates with 0.5 µg 28D4C10 in 100 µl PBS per well, hold overnight at 4° C.
2. Remove unbound 28D4C10 from wells by inverting plate to remove liquid. Wash 1× with $dH_2O$. Pat the plate on a paper towel to remove excess liquid.
3. Add 150 µl of Blocking Buffer to each well. Incubate for 30 min. at room temperature with shaking.
4. Wash plate 3× with deionized water, then once with TBST. Pat plate on a paper towel to remove excess liquid and bubbles.
5. Dilute lysate in HNTG (10 µg lysate/100 µl HNTG).
6. Add 100 µl of diluted lysate to each well. Shake at room temperature for 60 min.
7. Wash plates as described in Step 4.
8. Add 80 µl working kinase buffer mix to ELISA plate containing captured PDGFR.
9. Dilute test compound 1:10 in TBS in 96-well polypropylene plates.
10. Add 10 µl diluted test compound to ELISA plate. To control wells, add 10 µl TBS+10% DMSO. Incubate with shaking for 30 minutes at room temperature.
11. Add 10 µl ATP directly to all wells except negative control well (final well volume should be approximately 100 µl with 20 µM ATP in each well.) Incubate 30 minutes with shaking.
12. Stop reaction by adding 10 µl of EDTA solution to each well.
13. Wash 4× with deionized water, twice with TBST.
14. Add 100 µl anti-phosphotyrosine (1:3000 dilution in TBST) per well. Incubate with shaking for 30–45 min. at room temperature.
15. Wash as in Step 4.
16. Add 100 µl Biosource Goat anti-rabbit IgG peroxidase conjugate (1:2000 dilution in TBST) to each well. Incubate with shaking for 30 min. at room temperature.
17. Wash as in Step 4.
18. Add 100 µl of $ABTS/H_2O_2$ solution to each well.
19. Incubate 10 to 30 minutes with shaking. Remove any bubbles.
20. If necessary stop reaction with the addition of 100 µl 0.2 M HCl per well.
21. Read assay on Dynatech MR7000 ELISA reader with test filter at 410 nM and reference filter at 630 nM.

CDK2/Cyclin a Assay

This assay is used to measure the in vitro serine/threonine kinase activity of human cdk2/cyclin A in a Scintillation Proximity Assay (SPA).

Materials and Reagents.
1. Wallac 96-well polyethylene terephthalate (flexi) plates (Wallac Catalog # 1450-401).
2. Amersham Redivue [$\gamma^{33}$P]ATP (Amersham catalog #AH 9968).
3. Amersham streptavidin coated polyvinyltoluene SPA beads (Amersham catalog #RPNQ0007). The beads should be reconstituted in PBS without magnesium or calcium, at 20 mg/ml.
4. Activated cdk2/cyclin A enzyme complex purified from Sf9 cells (SUGEN, Inc.).
5. Biotinylated peptide substrate (Debtide). Peptide biotin-X-PKTPKKAKKL is dissolved in $dH_2O$ at a concentration of 5 mg/ml.
6. 20% DMSO in $dH_2O$.
7. Kinase buffer: for 10 ml, mix 9.1 ml $dH_2O$, 0.5 ml TRIS(pH 7.4), 0.2 ml 1M $MgCl_2$, 0.2 ml 10% NP40 and 0.02 ml 1M DTT, added fresh just prior to use.
8. 10 mM ATP in $dH_2O$.
9. 1M Tris, pH adjusted to 7.4 with HCl.
10. 1M $MgCl_2$.
11. 1M DTT.
12. PBS (Gibco Catalog # 14190-144).
13. 0.5M EDTA.

14. Stop solution: For 10 ml, mix 9.25 ml PBS, 0.05 ml 10 mM ATP, 0.1 ml 0.5 M EDTA, 0.1 ml 10% Triton X-100 and 1.5 ml of 50 mg/ml SPA beads.

Procedure:

1. Prepare solutions of test compounds at 4× the desired final concentration in 5% DMSO. Add 10 μL to each well. For positive and negative controls, use 10 μL 20% DMSO alone in wells.
2. Dilute the peptide substrate (deb-tide) 1:250 with dH$_2$O to give a final concentration of 0.02 mg/ml.
3. Mix 24 μL 0.1 mM ATP with 24 μCi γ$^{33}$p ATP and enough dH$_2$O to make 600 μL.
4. Mix diluted peptide and ATP solutions 1:1 (600 μL +600 μL per plate). Add 10 μL of this solution to each well.
5. Dilute 5 μL of cdk2/cyclin A solution into 2.1 ml 2× kinase buffer (per plate). Add 20 μL enzyme per well. For negative controls, add 20 μL 2× kinase buffer without enzyme.
6. Mix briefly on a plate shaker; incubate for 60 minutes.
7. Add 200 μL stop solution per well.
8. Let stand at least 10 min.
9. Spin plate at approx. 2300 rpm for 10–15 min.
10. Count plate on Trilux reader.

Met Transphosphorylation Assay

This assay is used to measure phosphotyrosine levels on a poly(glutamic acid:tyrosine, 4:1) substrate as a means for identifying agonists/antagonists of met transphosphorylation of the substrate.

Materials and Reagents:

1. Corning 96-well ELISA plates, Corning Catalog # 25805-96.
2. Poly(glu-tyr), 4:1, Sigma, Cat. No; P 0275.
3. PBS, Gibco Catalog # 450-1300EB
4. 50 mM HEPES
5. Blocking Buffer: Dissolve 25 g Bovine Serum Albumin, Sigma Cat. No A-7888, in 500 ml PBS, filter through a 4 μm filter.
6. Purified GST fusion protein containing the Met kinase domain, SUGEN, Inc.
7. TBST Buffer.
8. 10% aqueous (MilliQue H$_2$O) DMSO.
9. 10 mM aqueous (dH$_2$O) Adenosine-5'-triphosphate, Sigma Cat. No. A-5394.
10. 2× Kinase Dilution Buffer: for 100 ml, mix 10 mL 1M HEPES at pH 7.5 with 0.4 mL 5% BSA/PBS, 0.2 mL 0.1 M sodium orthovanadate and 1 mL 5M sodium chloride in 88.4 mL dH$_2$O.
11. 4× ATP Reaction Mixture: for 10 mL, mix 0.4 mL 1 M manganese chloride and 0.02 mL 0.1 M ATP in 9.56 mL dH$_2$O.
12. 4× Negative Controls Mixture: for 10 mL, mix 0.4 mL 1 M manganese chloride in 9.6 mL dH$_2$O.
13. NUNC 96-well V bottom polypropylene plates, Applied Scientific Catalog # S-72092
14. 500 mM EDTA.
15. Antibody Dilution Buffer: for 100 mL, mix 10 mL 5% BSA/PBS, 0.5 mL 5% Carnation® Instant Milk in PBS and 0.1 mL 0.1 M sodium orthovanadate in 88.4 mL TBST.
16. Rabbit polyclonal antophosphotyrosine antibody, SUGEN, Inc.
17. Goat anti-rabbit horseradish peroxidase conjugated antibody, Biosource, Inc.
18. ABTS Solution: for 1 L, mix 19.21 g citric acid, 35.49 g Na$_2$HPO$_4$ and 500 mg ABTS with sufficient dH$_2$O to make 1 L.
19. ABTS/H$_2$O$_2$: mix 15 mL ABST solution with 2 μL H$_2$O$_2$ five minutes before use.
20. 0.2 M HCl Procedure:

1. Coat ELISA plates with 2 μg Poly(Glu-Tyr) in 100 μL PBS, hold overnight at 4° C.
2. Block plate with 150 μL of 5% BSA/PBS for 60 min.
3. Wash plate twice with PBS then once with 50 mM Hepes buffer pH 7.4.
4. Add 50 μl of the diluted kinase to all wells. (Purified kinase is diluted with Kinase Dilution Buffer. Final concentration should be 10 ng/well.)
5. Add 25 μL of the test compound (in 4% DMSO) or DMSO alone (4% in dH$_2$O) for controls to plate.
6. Incubate the kinase/compound mixture for 15 minutes.
7. Add 25 μL of 40 mM MnCl$_2$ to the negative control wells.
8. Add 25 μL ATP/MnCl$_2$ mixture to the all other wells (except the negative controls). Incubate for 5 min.
9. Add 25 μL 500 mM EDTA to stop reaction.
10. Wash plate 3× with TBST.
11. Add 100 μL rabbit polyclonal anti-Ptyr diluted 1:10,000 in Antibody Dilution Buffer to each well. Incubate, with shaking, at room temperature for one hour.
12. Wash plate 3× with TBST.
13. Dilute Biosource HRP conjugated anti-rabbit antibody 1:6,000 in Antibody Dilution buffer. Add 100 μL per well and incubate at room temperature, with shaking, for one hour.
14. Wash plate 1× with PBS.
15. Add 100 μl of ABTS/H$_2$O$_2$ solution to each well.
16. If necessary, stop the development reaction with the addition of 100 μl of 0.2M HCl per well.
17. Read plate on Dynatech MR7000 ELISA reader with the test filter at 410 nM and the reference filter at 630 nM.

IGF-1 Transphosphorylation Assay

This assay is used to measure the phosphotyrosine level in poly(glutamic acid:tyrosine, 4:1) for the identification of agonists/antagonists of gst-IGF-1 transphosphorylation of a substrate.

Materials and Reagents:

1. Corning 96-well ELISA plates.
2. Poly(Glu-Tyr), 4:1, Sigma Cat. No. P 0275.
3. PBS, Gibco Catalog # 450-1300EB.
4. 50 mM HEPES
5. TBB Blocking Buffer: for 1 L, mix 100 g BSA, 12.1 g TRIS (pH 7.5), 58.44 g sodium chloride and 10 mL 1% TWEEN-20.
6. Purified GST fusion protein containing the IGF-1 kinase domain (SUGEN, Inc.)
7. TBST Buffer: for 1 L, mix 6.057 g Tris, 8.766 g sodium chloride and 0.5 ml TWEEN-20 with enough dH$_2$O to make 1 liter.
8. 4% DMSO in Milli-Q H$_2$O.
9. 10 mM ATP in dH$_2$O.
10. 2× Kinase Dilution Buffer: for 100 mL, mix 10 mL 1 M HEPES (pH 7.5), 0.4 mL 5% BSA in dH$_2$O, 0.2 mL 0.1 M sodium orthovanadate and 1 mL 5 M sodium chloride with enough dH$_2$O to make 100 mL.
11. 4× ATP Reaction Mixture: for 10 mL, mix 0.4 mL 1 M MnCl$_2$ and 0.008 mL 0.01 M ATP and 9.56 mL dH$_2$O.
12. 4× Negative Controls Mixture: mix 0.4 mL 1 M MnCl$_2$ in 9.60 mL dH$_2$O.

13. NUNC 96-well V bottom polypropylene plates.
14. 500 mM EDTA in dH$_2$O.
15. Antibody Dilution Buffer: for 100 mL, mix 10 mL 5% BSA in PBS, 0.5 mL 5% Carnation Instant Non-fat Milk in PBS and 0.1 mL 0.1 M sodium orthovanadate in 88.4 mL TBST.
16. Rabbit Polyclonal antiphosphotyrosine antibody, SUGEN, Inc.
17. Goat anti-rabbit HRP conjugated antibody, Biosource.
18. ABTS Solution.
20. ABTS/H$_2$O$_2$: mix 15 mL ABTS with 2 µL H$_2$O$_2$ 5 minutes before using.
21. 0.2 M HCl in dH$_2$O.

Procedure:
1. Coat ELISA plate with 2.0 µg/well Poly(Glu, Tyr), 4:1 (Sigma P0275) in 100 µl PBS. Store plate overnight at 4° C.
2. Wash plate once with PBS.
3. Add 100 µl of TBB Blocking Buffer to each well. Incubate plate for 1 hour with shaking at room temperature.
4. Wash plate once with PBS, then twice with 50 mM Hepes buffer pH 7.5.
5. Add 25 µL of test compound in 4% DMSO (obtained by diluting a stock solution of 10 mM test compound in 100% DMSO with dH$_2$O) to plate.
6. Add 10.0 ng of gst-IGF-1 kinase in 50 µl Kinase Dilution Buffer to all wells.
7. Start kinase reaction by adding 25 µl 4× ATP Reaction Mixture to all test wells and positive control wells. Add 25 µl 4× Negative Controls Mixture to all negative control wells. Incubates for 10 minutes, with shaking, at room temperature.
8. Add 25 µl 0.5M EDTA (pH 8.0) to all wells.
9. Wash plate 4× with TBST Buffer.
10. Add rabbit polyclonal anti-phosphotyrosine antisera at a dilution of 1:10,000 in 100 µl Antibody Dilution Buffer to all wells. Incubate, with shaking, at room temperature for 1 hour.
11. Wash plate as in step 9.
12. Add 100 µL Biosource anti-rabbit HRP at a dilution of 1:10,000 in Antibody dilution buffer to all wells. Incubate, with shaking, at room temperature for 1 hour.
13. Wash plate as in step 9, follow with one wash with PBS to remove bubbles and excess Tween-20.
14. Develop by adding 100 µl/well ABTS/H$_2$O$_2$ to each well.
15. After about 5 minutes, read on ELISA reader with test filter at 410 nm and referenced filter at 630 nm.

BrdU Incorporation Assays

The following assays use cells engineered to express a selected receptor and then evaluate the effect of a compound of interest on the activity of ligand-induced DNA synthesis by determining BrdU incorporation into the DNA.

The following materials, reagents and procedure are general to each of the following BrdU incorporation assays. Variances in specific assays are noted.

General Materials and Reagents:
1. The appropriate ligand.
2. The appropriate engineered cells.
3. BrdU Labeling Reagent: 10 mM, in PBS, pH7.4(Roche Molecular Biochemicals, Indianapolis, Ind.).
4. FixDenat: fixation solution (Roche Molecular Biochemicals, Indianapolis, Ind.).
5. Anti-BrdU-POD: mouse monoclonal antibody conjugated with peroxidase (Chemicon, Temecula, Calif.).
6. TMB Substrate Solution: tetramethylbenzidine (TMB, ready to use, Roche Molecular Biochemicals, Indianapolis, Ind.).
7. PBS Washing Solution: 1×PBS, pH 7.4.
8. Albumin, Bovine (BSA), fraction V powder (Sigma Chemical Co., USA).

General Procedure:
1. Cells are seeded at 8000 cells/well in 10% CS, 2 mM Gln in DMEM, in a 96 well plate. Cells are incubated overnight at 37° C. in 5% CO$_2$.
2. After 24 hours, the cells are washed with PBS, and then are serum-starved in serum free medium (0% CS DMEM with 0.1% BSA) for 24 hours.
3. On day 3, the appropriate ligand and the test compound are added to the cells simultaneously. The negative control wells receive serum free DMEM with 0.1% BSA only; the positive control cells receive the ligand but no test compound. Test compounds are prepared in serum free DMEM with ligand in a 96 well plate, and serially diluted for 7 test concentrations.
4. After 18 hours of ligand activation, diluted BrdU labeling reagent (1:100 in DMEM, 0.1% BSA) is added and the cells are incubated with BrdU (final concentration is 10 µM) for 1.5 hours.
5. After incubation with labeling reagent, the medium is removed by decanting and tapping the inverted plate on a paper towel. FixDenat solution is added (50 µl/well) and the plates are incubated at room temperature for 45 minutes on a plate shaker.
6. The FixDenat solution is removed by decanting and tapping the inverted plate on a paper towel. Milk is added (5% dehydrated milk in PBS, 200 µl/well) as a blocking solution and the plate is incubated for 30 minutes at room temperature on a plate shaker.
7. The blocking solution is removed by decanting and the wells are washed once with PBS. Anti-BrdU-POD solution is added (1:200 dilution in PBS, 1% BSA, 50 µl/well) and the plate is incubated for 90 minutes at room temperature on a plate shaker.
8. The antibody conjugate is removed by decanting and rinsing the wells 5 times with PBS, and the plate is dried by inverting and tapping on a paper towel.
9. TMB substrate solution is added (100 µl/well) and incubated for 20 minutes at room temperature on a plate shaker until color development is sufficient for photometric detection.
10. The absorbance of the samples are measured at 410 nm (in "dual wavelength" mode with a filter reading at 490 nm, as a reference wavelength) on a Dynatech ELISA plate reader.

EGF-Induced BrdU Incorporation Assay

Materials and Reagents:
1. Mouse EGF, 201 (Toyobo Co., Ltd., Japan).
2. 3T3/EGFRc7.

Remaining Materials and Reagents and Procedure, as above.

PDGF-Induced BrdU Incorporation Assay

Materials and Reagents:
1. Human PDGF B/B (Boehringer Mannheim, Germany).
2. 3T3/EGFRc7.

Remaining Materials and Reagents and Procedure, as above.

FGF-Induced BrdU Incorporation Assay

Materials and Reagents:
1. Human FGF2/bFGF (Gibco BRL, USA).
2. 3T3c7/EGFr

Remaining Materials and Reagents and Procedure, as above.

IGF1-Induced BrdU Incorporation Assay

Materials and Reagents:
1. Human, recombinant (G511, Promega Corp., USA)
2. 3T3/IGF1r.

Remaining Materials and Reagents and Procedure, as above.

Src Transphosphorylation Assay

This assay is used to screen for inhibitors of the tyrosine kinase Src.

Materials and Reagents:
1. Coating buffer: PBS containing sodium azide (0.2 mg/ml).
2. 1% w/v BSA in PBS.
3. Wash buffer: PBS containing 0.05% v/v Tween 20 (PBS-TWEEN)
4. 500 mM HEPES pH7.4.
5. ATP (40 µM)+MgCl$_2$ (80 mM) in distilled water.
6. MgCl$_2$ (80 mM) in distilled water (for no ATP blanks).
7. Test compounds, 10 mM in DMSO.
8. Assay Buffer: 100 mM HEPES, pH 7.4, containing 2 mM DTT, 0.2 mM sodium orthovanadate and 0.2 mgs/ml BSA.
9. Partially purified recombinant human Src (UBI (14–117)
10. Anti-phosphotyrosine (SUGEN rabbit polyclonal anti-PY).
11. HRP-linked goat anti-rabbit Ig (Biosource International #6430)
12. HRP substrate ABTS or Pierce Peroxidase substrate.
13. Corning ELISA plates.

Procedure:
1. Coat plates with 100 µl of 20 µg/ml poly(Glu-Tyr) (Sigma Cat. No. P0275) containing 0.01% sodium azide. Hold overnight at 4° C.
2. Block with 1% BSA at 100 µl/well for one hour at room temperature.
3. Plate test compounds (10 mM in DMSO) at 2 µl/well on a Costar plate ready for dilution with dH$_2$O and plating to reaction plates.
4. Dilute Src kinase 1:10,000 in Reaction Buffer, for 5 plates prepare 25 ml as follows: 2.5 mls 1 M HEPES pH7.4 (stored sterile at 4° C.), 21.85 ml distilled water, 0.1 ml 5% BSA, 0.5 ml 10 mM sodium orthovanadate (stored sterile at 4° C.), 50 µl 1.0M DTT (stored frozen at −20° C.), and 2.5 µl Src Kinase (stored frozen at −80° C.).
5. Add 48 µl of distilled water to the 2 µl of each compound in the dilution plate then add 25 µl/well of this to the reaction plate.
6. Add 50 µl of HRP to each reaction buffer well and then 25 µl ATP-MgCl$_2$/well (MgCl$_2$ only to no ATP blanks). Incubate at room temperature for 15 minutes on plate shaker. Stop reaction by adding 25 µl of 0.5M EDTA to each well.
7. Wash 4× with PBS-TWEEN.
8. Add 100 µl anti-phosphotyrosine (1:10,000 of anti-pTyr serum or 1:3,000 of 10% glycerol diluted PA-affinity purified antibody) in PBS-TWEEN containing 0.5% BSA, 0.025% Non-fat milk powder and 100 µM sodium orthovanadate. Incubate with continuous shaking at room temperature for one hour.
9. Wash plates 4× with PBS-TWEEN.
10. Add 100 µl HRP-linked Ig (1:5,000) in PBS-TWEEN containing 0.5% BSA, 0.025% Non-fat milk powder, 100 µM sodium orthovanadate. Incubate with shaking at room temperature for one hour.
11. Wash plates 4× with PBS-TWEEN and then once with PBS.
12. Develop plate using ABTS or other peroxidase substrate.

Cell Cycle Analysis:

A431 cells in standard growth medium are exposed to a desired concentration of a test compound for 20–24 hours at 37° C. The cells are then collected, suspended in PBS, fixed with 70% ice-cold methanol and stained with propidium iodide. The DNA content is then measured using a FACScan flow cytometer. Cell cycle phase distribution can then be estimated using CellFIT software (Becton-Dickinson).

HUV-EC-C Assay

This assay is used to measure a compound's activity against PDGF-R, FGF-R, VEGF, aFGF or Flk-1/KDR, all of which are naturally expressed by HUV-EC cells.

DAY 0
1. Wash and trypsinize HUV-EC-C cells (human umbilical vein endothelial cells, (American Type Culture Collection, catalogue no. 1730 CRL). Wash with Dulbecco's phosphate-buffered saline (D-PBS, obtained from Gibco BRL, catalogue no. 14190-029) 2 times at about 1 ml/10 cm$^2$ of tissue culture flask. Trypsinize with 0.05% trypsin-EDTA in non-enzymatic cell dissociation solution (Sigma Chemical Company, catalogue no. C-1544). The 0.05% trypsin is made by diluting 0.25% trypsin/1 mM EDTA (Gibco, catalogue no. 25200-049) in the cell dissociation solution. Trypsinize with about 1 ml/25–30 cm$^2$ of tissue culture flask for about 5 minutes at 37° C. After cells have detached from the flask, add an equal volume of assay medium and transfer to a 50 ml sterile centrifuge tube (Fisher Scientific, catalogue no. 05-539-6).
2. Wash the cells with about 35 ml assay medium in the 50 ml sterile centrifuge tube by adding the assay medium, centrifuge for 10 minutes at approximately 200×g, aspirate the supernatant, and resuspend with 35 ml D-PBS. Repeat the wash two more times with D-PBS, resuspend the cells in about 1 ml assay medium/15 cm$^2$ of tissue culture flask. Assay medium consists of F12K medium (Gibco BRL, catalogue no. 21127-014) and 0.5% heat-inactivated fetal bovine serum. Count the cells with a Coulter Counter® (Coulter Electronics, Inc.) and add assay medium to the cells to obtain a concentration of 0.8–1.0×10$^5$ cells/ml.
3. Add cells to 96-well flat-bottom plates at 100 µl/well or 0.8–1.0×10$^4$ cells/well, incubate ~24 h at 37° C., 5% CO$_2$.

DAY 1
1. Make up two-fold test compound titrations in separate 96-well plates, generally 50 µM on down to 0 µM. Use the same assay medium as mentioned in day 0, step 2 above. Titrations are made by adding 90 µl/well of test compound at 200 µM (4× the final well concentration) to the top well of a particular plate column. Since the stock test compound is usually 20 mM in DMSO, the 200 µM drug concentration contains 2% DMSO.

A diluent made up to 2% DMSO in assay medium (F12K+0.5% fetal bovine serum) is used as diluent for the test compound titrations in order to dilute the test compound but keep the DMSO concentration constant. Add this diluent to the remaining wells in the column at 60 µl/well. Take 60 µl from the 120 µl of 200 µM test compound dilution in the top well of the column and mix with the 60 µl in the second well of the column. Take 60 µl from this well and mix with the 60 µl in the third well of the column, and so on until two-fold titrations are completed. When the next-to-the-last well is mixed, take 60 µl of the 120 µl in this well and discard it. Leave the last well with 60 µl of DMSO/media diluent as a non-test compound-containing control. Make 9 columns of titrated test compound, enough for triplicate wells each for: (1) VEGF (obtained from Pepro Tech Inc., catalogue no. 100-200, (2) endothelial cell growth factor (ECGF) (also known as acidic fibroblast growth factor, or aFGF) (obtained from Boehringer Mannheim Biochemica, catalogue no. 1439 600), or, (3) human PDGF B/B (1276-956, Boehringer Mannheim, Germany) and assay media control. ECGF comes as a preparation with sodium heparin.

2. Transfer 50 µl/well of the test compound dilutions to the 96-well assay plates containing the $0.8–1.0 \times 10^4$ cells/100 µl/well of the HUV-EC-C cells from day 0 and incubate ~2 h at 37° C., 5% $CO_2$.

3. In triplicate, add 50 µl/well of 80 µg/ml VEGF, 20 ng/ml ECGF, or media control to each test compound condition. As with the test compounds, the growth factor concentrations are 4× the desired final concentration. Use the assay media from day 0 step 2 to make the concentrations of growth factors. Incubate approximately 24 hours at 37° C., 5% $CO_2$. Each well will have 50 µl test compound dilution, 50 µl growth factor or media, and 100 µl cells, which calculates to 200 µl/well total. Thus the 4× concentrations of test compound and growth factors become 1× once everything has been added to the wells.

DAY 2

1. Add $^3$H-thymidine (Amersham, catalogue no. TRK-686) at 1 µCi/well (10 µl/well of 100 µCi/ml solution made up in RPMI media+10% heat-inactivated fetal bovine serum) and incubate ~24 h at 37° C., 5% $CO_2$. RPMI is obtained from Gibco BRL, catalogue no. 11875-051.

DAY 3

1. Freeze plates overnight at −20° C.

DAY 4

Thaw plates and harvest with a 96-well plate harvester (Tomtec Harvester 96®) onto filter mats (Wallac, catalogue no. 1205-401), read counts on a Wallac Betaplate™ liquid scintillation counter.

In Vivo Animal Models

Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, Acta Pathol. Microbial. Scand. 77:758–760), many different human tumor cell lines (e.g., mammary, lung, genitourinary, gastro-intestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC # CCL 107), A375 cells (melanoma, ATCC # CRL 1619), A431 cells (epidermoid carcinoma, ATCC # CRL 1555), Calu 6 cells (lung, ATCC # HTB 56), PC3 cells (prostate, ATCC # CRL 1435), SKOV3TP5 cells, S114 (NIH3T3 fibroblast cell line genetically engineered for cMet and HGF expressions from NCI), U-87MG (human malignant glioma, ATCC HTB 14) and NIH 3T3 fibroblasts genetically engineered to overexpress EGFR, PDGFR, IGF-1R or any other test kinase. The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%-10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hindflank of the mice (8–10 mice per group, $2–10\times10^6$ cells/animal). Tumor growth is measured over 3 to 6 weeks using venier calipers. Tumor volumes are calculated as a product of length×width×height unless otherwise indicated. P values are calculated using the Students t-test. Test compounds in 50-100 µL excipient (DMSO, or VPD:D5W) can be delivered by IP injection at different concentrations generally starting at day one after implantation.

Tumor Invasion Model

The following tumor invasion model has been developed and may be used for the evaluation of therapeutic value and efficacy of the compounds identified to selectively inhibit KDR/FLK-1 receptor.

Procedure 8 week old nude mice (female) (Simonsen Inc.) are used as experimental animals. Implantation of tumor cells can be performed in a laminar flow hood. For anesthesia, Xylazine/Ketamine Cocktail (100 mg/kg ketamine and 5 mg/kg Xylazine) are administered intraperitoneally. A midline incision is done to expose the abdominal cavity (approximately 1.5 cm in length) to inject $10^7$ tumor cells in a volume of 100 µl medium. The cells are injected either into the duodenal lobe of the pancreas or under the serosa of the colon. The peritoneum and muscles are closed with a 6–0 silk continuous suture and the skin is closed by using wound clips. Animals are observed daily.

Analysis

After 2–6 weeks, depending on gross observations of the animals, the mice are sacrificed, and the local tumor metastases to various organs (lung, liver, brain, stomach, spleen, heart, muscle) are excised and analyzed (measurement of tumor size, grade of invasion, immunochemistry, in situ hybridization determination, etc.).

Met Phosphorylation—Cellular Assay

Materials and Reagents:
1. Falcon 10 cm culture dishes.
2. A549 lung carcinoma cells.
3. F12K growth medium (with 2% FBS+2 mM glutamine.
4. F12K assay medium (with 0.1% BSA).
5. Fisher cell scrapers.
6. Lysis buffer (HNTG, 1 mM sodium orthovanidate, 1 mM PMSF and 2 mM sodium fluoride).
7. 1.5 ml Eppendorf tubes.
8. Eppendorf microcentrifuge.
9. BCA assay reagents A and B (#23223 and 23224, Pierce).
10. Sample tube rotator.
11. Gel blot container rotator.
12. 5× sample buffer.
13. Novex pre-cast tris-glycine 8% acrylamide gels.
14. Bio-Rad electrophoresis chamber.
15. SDS-PAGE buffer.
16. TBS (pH 7.6)+0.1% Triton X-100 (TBST), with and wihtout 5% milk.
17. Western blot transfer buffer.
18. Osmonics nitrocellulose paper.
19. Bio-Rad Transblot paper.
20. Gel transfer apparatus.
21. Anti-phosphotyrosine (mouse monoclonal).
22. Bio-Rad Kaleidoscope Prestained Standards (161-0324).
23. Anti-h-met (C-28) rabbit polyclonal, conjugated and non-conjugated with agarose (#sc-161 AC and sc-161, Santa Cruz Biotechnology, Inc.).
24. Donkey and anti-rabbit lg-HRP (NA 934, Amersham).
25. Sheet anti-mouselg-HRP (NA 931, Amersham).
26. SuperSignal West Pico Chemiluminescent Substrate (#34080, Pierce).
27. Saran Wrap.
28. Kodak BioMax exposure cassette.
29. Fuji X-ray film.
30. Kodak film developer.

Procedure:
1. Plate cells in 10 cm dishes with growth medium with 2% FBS+2 mM glutamine. Grow to near confluency.
2. Serum starve cells overnight in assay medium with 0.1% BSA.
3. Add drug to the plates, one dose per plate, usually in a 2-flod titration. Add asay medium (with the same DMSO concentration as the drugs) for no drug.
4. Incubate plates 4–5 hours with the drug, then add HG, 50 ng/ml for 10 minutes.
5. Wash plates once with PBS, add 400 µl lysis buffer, and scrape off the cells. Collect in 1.5 ml Eppendorf tubes.
6. After about 10–20 minutes in the lysis buffer, centrifuge lysates in a microcentrifuger at full speed (14,000 g) and collect the supernatants in a separate Eppendorf tube.
7. Determine protein concentration with the BCA assay reagents.
8. Adjust sample concentration to 0.5 mg protein in 0.4 ml using lysis buffer.
9. Add 15 µl anti-h-met AC for immunoprecipitation, rotate samples for 2 hours at 4° C.
10. Wash samples 3 times with lysis buffer and resuspend in 35 µl 5× sample buffer.
11. Boil sample at 100° C. for 10 minutes and microcentrifuge at highest setting for 30 minutes to pellet the agarose beads.
12. Load 15 µl each to 2 gels, one for anti-phosphorylation and the other for anti-h-met. Also load 10 µl of prestained standards, one lane per gel.
13. Run gel around 100–125 V, then transfer gel to nitrocellulose either overnight at 70 mAmps or 1 hour at 500 mAmps.
14. Block membranes on rotator for 1 hour in TBS+0.1% Triton X-100 (TBST)+5% PBS. All steps from this point are at room temperature unless otherwise unless otherwise noted.
15. Add 0.8 µg/ml antiphosphotyrosine and 0.25 µg/ml anti-h-met on rotator either for 2 hours or overnight.
16. Wash membranes 3 times 5 minutes each in TBST on rotator.
17. Add HRP-conjugated antibodies )sheep anti-mouse for the antiphosphotyroeins; donkey anti-rabbit for the nati-h-met) at 1:5000 for approximately 45 minutes on rotator.
18. Wash membranes 3 times for 5 minutes each in TBST on rotator.
19. Add the 2 reagents in th3e SuperSignal kit together in equal volumes (3 ml+3 ml for each blot), rotate for 1–2 minutes.
20. Wrap blots in Saran Wrap and tape securely inside the exposure cassette.
21. In the darkroom with only the safety light on, place a sheet of film inside the cassette. After an allotted time, remove film and place in the developer machine for automatic processing. Experiment with the exposure time to get proper exposure.

ZC1 Scintillation Proximity Assay

The Scintillation Proximity assay (SPA) is used to analyze the protein serine/threonine kinase activity of ZC1 in vitro to screen for inhibitors of ZC1 in a homogeneous assay. The assay described below is amenable for high throughput screening of ZC1 Inhibitors.

Materials and Solutions:
1. Wallac 96-well polyethylene terephthalate (flexi) plates (Wallac Catalog #1450-401)
2. NEN Easy-Tide [$\gamma$33P] ATP (NEN Catalog #NEG602H)
3. Amersham streptavidin coated polyvinyltoluene SPA beads (Amersham catalog #NIF 107)—Reconstitute beads in PBS without magnesium or calcium, at 50 mg/mL. Store reconstituted beads at 4° C. (To achieve optimal counts, it is important that excess streptavidin SPA bead should be present in order to bind all of the biotinylated molecules in the assay.) Activated ZC1 enzyme purified from Sf9 cells—Final concentration of 300 ng/well.
4. Peptide substrate #902B (biotin-KRTLRRKRTLR-RKRTLRR)—Final concentration of 0.5 µM/well (2×Km)

Procedure:
1. Prepare solutions of inhibitors at 5× the desired final concentration in 5% DMSO. Add 10 µL to each well of the flexiplate. For positive and negative controls, add 10 µL 5% DMSO.
2. Prepare ATP mix as shown above (2.1 ml of ATP mix is sufficient for one assay plate). Add 20 µL to all wells.

3. Add 20 μL of 5M EDTA to negative control wells.

4. Prepare the enzyme solution in 2.5× kinase buffer (50 mM HEPES pH 7.4, 12.5 mM MnCl$_2$, 500 mM NaCl, and 1 mM DTT. The final enzyme concentration will be 0.30 μg/well (For example, given a 0.5 mg/mL stock, add 302 μL ZC1 enzyme to 10 mL Kinase Buffer.) Add 20 μL per well to start the reaction.

5. Allow kinase reaction to proceed at room temperature for 60 minutes.

6. To each well, add 200 μL of a stop solution containing 0.05 mM ATP, 5 mM EDTA, 0.1% Triton x-100, and 5 mg per ml Amersham streptavidin-coated polyvinyltoluene SPA beads (Cat # NIF 1077) in PBS. Incubate for 15 minutes.

7. Spin plate at 2300 rpm for 15 min.

8. Count plate on Trilux reader using SPA flexiplate protocol (including quench curve).

Aurora2 Scintillation Proximity assay

The Scintillation Proximity assay (SPA) is used to analyze the protein serine/threonine kinase activity of Aurora2 in vitro to screen for inhibitors of Aurora2 in a homogeneous assay. The assay described below is amenable for high throughput screening of Aurora2 Inhibitors.

Materials and Solutions:

1. Wallac 96-well polyethylene terephthalate (flexi) plates (Wallac Catalog #1450-401)

2. NEN Easy-Tide [γ$^{33}$P] ATP (NEN Catalog #NEG602H)

3. Amersham streptavidin coated polyvinyltoluene SPA beads (Amersham catalog #NIF 107)—Reconstitute beads in PBS without magnesium or calcium, at 50 mg/mL. Store reconstituted beads at 4° C. (To achieve optimal counts, it is important that excess streptavidin SPA bead should be present in order to bind all of the biotinylated molecules in the assay.)

4. Enzyme: GST-Aurora2 enzyme purified from BL21 cells. 1.0 mg/ml; 500 μl aliquots. Use 0.125 mg/assay well.

5. Biotinylated peptidesubstrate: SUGEN peptide #800A. Biotin-LC-LC-LRRWSLGLRRWSLGLRRWSLGLR-RWSLG dissolved in DMSO at a concentration of 10 mg/ml. Stored at −20° C. in 500 μl aliquots-Final concentration of 0.012 mlg/well (2×Km).

Procedure:

1. Prepare solutions of inhibitors at 5× the desired final concentration in 5% DMSO. Add 10 μL to each well of the flexiplate. For positive and negative controls, add 10 μL 5% DMSO.

2. Prepare ATP mix as shown above (2.1 ml of ATP mix is sufficient for one assay plate). Add 20 μL to all wells.

| Reagent | Stock Solutio | Amount per 10 ml | Working Concentration | Final Concentration |
|---|---|---|---|---|
| dH$_2$O | | 9.94 ml | | |
| ATP | 10 mM | 0.015 ml | 0.015 mM | 0.006 mM |
| Peptide 800A | 10 mg/ml | 0.03 ml | 0.03 mg/ml | 0.012 mg/ml |
| $^{33}$P ATP | 10 μCi/μl | 0.0165 ml | 16.5 μCi/ml | 6.6 μCi/μl |

3. Add 20 μL of 5M EDTA to negative control wells.

4. Prepare the enzyme solution in 2.5× kinase buffer (50 mM HEPES pH 7.4, 12.5 mM MnCl$_2$, 500 mM NaCl, and 1 mM DTT. The final enzyme concentration will be 0.125 μg/well. Add 20 μL per well to start the reaction.

5. Allow kinase reaction to proceed at room temperature for 60 minutes.

6. To each well, add 200 μL of a stop solution containing 0.05 mM ATP, 5 mM EDTA, 0.1% Triton x-100, and 5 mg per ml Amersham streptavidin-coated polyvinyltoluene SPA beads (Cat# NIF 1077) in PBS. Incubate for 15 minutes.

7. Spin plate at 2300 rpm for 15 min.

8. Count plate on Trilux reader using SPA flexiplate protocol.

ADDITIONAL ASSAYS

Additional assays which may be used to evaluate the compounds of this invention include, without limitation, a bio-flk-1 assay, an EGF receptor-HER2 chimeric receptor assay in whole cells, a bio-src assay, a bio-lck assay and an assay measuring the phosphorylation function of raf. The protocols for each of these assays may be found in U.S. application Ser. No. 09/099,842, which is incorporated by reference, including any drawings, herein. Additionally, U.S. Pat. No. 5,792,783, filed June 5, 1996 and U.S. application Ser. No. 09/322,297, filed May 28, 1999 are incorporated by reference as if fully set forth herein.

Table 1, below, shows the IC$_{50}$ values obtained for a number of compounds of the preferred embodiments of the invention.

| Compound | Example No. | FGFR IC$_{50}$ (μM) |
|---|---|---|
| (structure) | 1 | 0.079 |

| Compound | Example No. | FGFR IC$_{50}$ (μM) |
|---|---|---|
| (2,6-dichlorobenzylsulfonyl-substituted indolinone fused with cyclopenta-pyrrole bearing ethyl ester and methyl groups) | 2 | 2.5 |
| (N-methylsulfamoyl-substituted indolinone fused with cyclopenta-pyrrole bearing ethyl ester and methyl groups) | 3 | 0.6 |
| (N-methylsulfamoyl-substituted indolinone fused with cyclopenta-pyrrole bearing methyl group) | 4 | 0.025 |
| (N-methylsulfamoyl-substituted indolinone fused with cyclopenta-pyrrole bearing carboxylic acid and methyl groups) | 5 | 0.022 |
| (methylsulfonyl-substituted indolinone fused with cyclopenta-pyrrole bearing ethyl ester and methyl groups) | 6 | 14.5 |

| Compound | Example No. | FGFR IC$_{50}$ (µM) |
|---|---|---|
| | 7 | >20 |
| | 8 | >20 |
| | 9 | 0.53 |
| | 10 | <0.018 |

-continued
| Compound | Example No. | FGFR IC$_{50}$ (μM) |
|---|---|---|
| 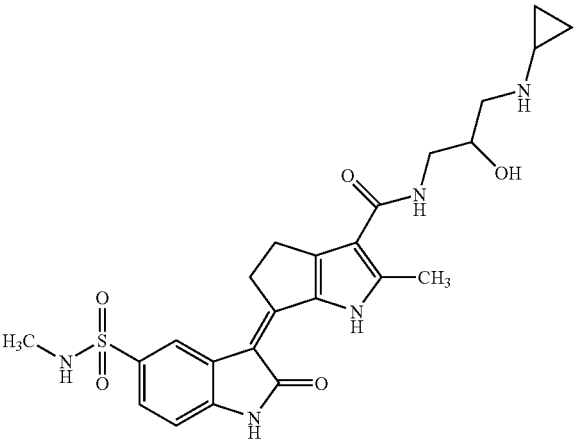 | 11 | 0.02 |
| 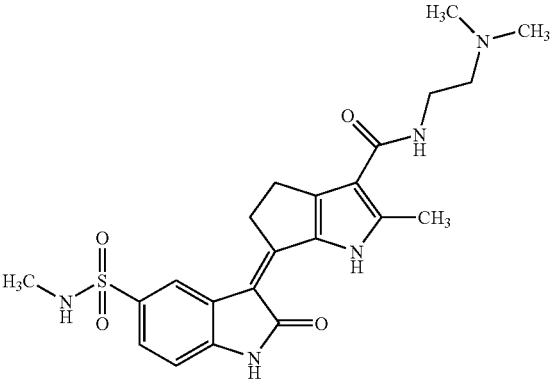 | 12 | 0.017 |
| Chiral<br />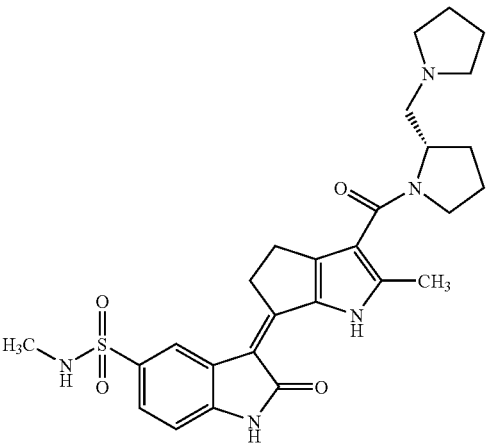 | 13 | 0.015 |
| 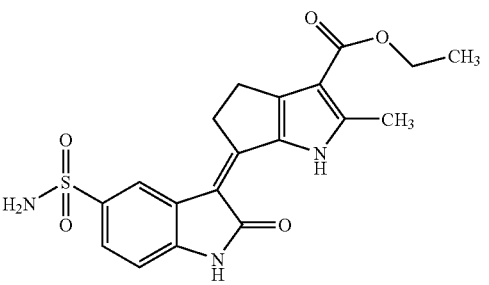 | 14 | 0.1 |

-continued
| Compound | Example No. | FGFR IC$_{50}$ (μM) |
|---|---|---|
| 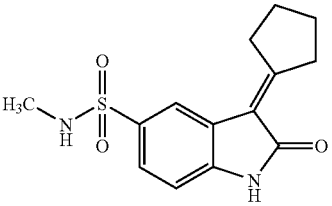 | 15 | >20 |
| 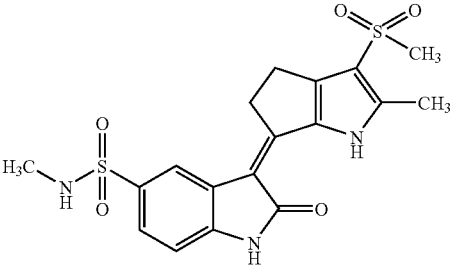 | 16 | 0.015 |
| 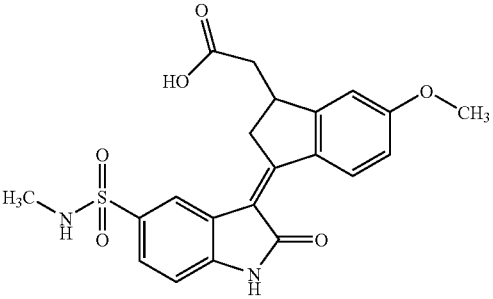 | 17 | 0.04 |
| Chiral<br>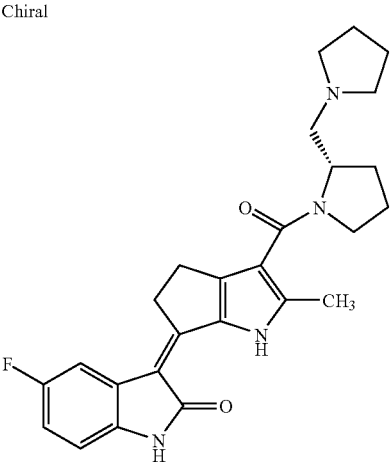 | 18 | 0.08 |

-continued

| Compound | Example No. | FGFR IC$_{50}$ (μM) |
|---|---|---|
| Chiral | 19 | 0.21 |
| Chiral | 20 | 0.48 |
| Chiral | 21 | 1.9 |

| Compound | Example No. | FGFR IC$_{50}$ (µM) |
|---|---|---|
| Chiral [structure] | 22 | 2.07 |
| Chiral [structure] | 23 | 0.23 |

One skilled in the art would also readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.

What is claimed is:

1. A compound of the Formula:

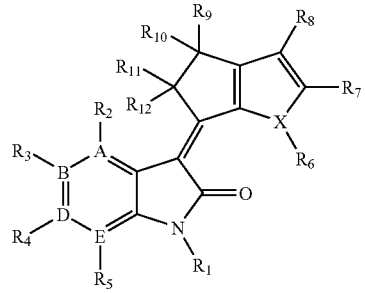

wherein A, B, D and E are each carbon;

$R_1$ and $R_6$ are each H;

$R_2$, $R_3$, $R_4$, $R_5$ and $R_7$ are each independently selected from the group consisting of H, alkyl, cycloalkyl, alkenyl, alkynyl, aryl, trihaloalkyl, hydroxy, alkoxy, aryloxy, mercapto, alkylthio, arylthio, —$SOR_{13}$, —$SO_2R_{13}$, —$SO_2NR_{13}R_{14}$, $R_{14}SO_2N(R_{13})$—, N-trihalomethanesulfonamido, —$C(O)R_{15}$, —$C(O)OR_{15}$, $R_{15}C(O)O$—, cyano, nitro, halo, cyanato, isocyanato, isocyanato, thiocyanato, isothiocyanato, —$OC(O)NR_{13}R_{14}$, $R_{14}OC(O)NR_{13}$—, —$OC(S)NR_{13}R_{14}$, $R_{14}OC(S)NR_{13}$—, —$C(O)NR_{13}R_{14}$, $R_{14}C(O)NR_{13}$— and —$NR_{13}R_{14}$;

$R_8$ is selected from the group consisting of H, alkyl, cycloalkyl, alkenyl, alkynyl, aryl, heteroaryl, trihaloalkyl, heteroalicyclic, hydroxy, alkoxy, aryloxy, mercapto, alkylthio, arylthio, —$SOR_{13}$, —$SO_2R_{13}$, —$SO_2NR_{13}R_{14}$, $R_{14}SO_2N(R_{13})$—, N-trihalomethanesulfonamido, —$C(O)R_{15}$, —$C(O)OR_{15}$, $R_{15}C(O)O$—, cyano, nitro, halo, cyanato, isocyanato, isocyanato, thiocyanato, isothiocyanato, —$OC(O)NR_{13}R_{14}$, $R_{14}OC(O)NR_{13}$—, —$OC(S)NR_{13}R_{14}$, $R_{14}OC(S)NR_{13}$—, —$C(O)NR_{13}R_{14}$, $R_{14}C(O)NR_{13}$— and —$NR_{13}R_{14}$;

$R_{13}$ and $R_{14}$ are each independently selected from the group consisting of H, alkyl, cycloalkyl, aryl, alkylaryl, arylalkyl, heteroaryl, heteroalicyclic, —$C(O)R_{15}$, acetyl, —$SO_2R_{15}$ and —$(CH_2)_nNR_{13}R_{14}$;

$R_{15}$ is selected from the group consisting of H, alkyl, cycloalkyl, aryl, heteroaryl and heteroalicyclic;

$R_9$, $R_{10}$, $R_{11}$ and $R_{12}$ are each independently selected from the group consisting of H, alkyl, cycloalkyl, alkenyl, alkynyl, aryl, trihaloalkyl, halo, cyano, hydroxy, alkoxy, aryloxy, alkylthio, arylthio, —$SO_2R_{15}$, —$S(O)R_{15}$, —$(CH_2)_nC(O)OR_{15}$, cyanato, isocyanato, thiocyanato, isothiocyanato, —$C(O)NR_{13}R_{14}$, $R_{14}C(O)NR_{13}$— and —$NR_{13}R_{14}$;

n is an integer from 0 to 20; and

X is nitrogen;

or a prodrug or pharmaceutically acceptable salt thereof.

2. The compound of claim 1, wherein $R_2$, $R_3$, $R_4$, $R_5$, $R_7$ and $R_8$ are each independently selected from the group consisting of H, alkyl, aryl, hydroxy, alkoxy,—$SOR_{13}$, —$SO_2R_{13}$, —$SO_2NR_{13}R_{14}$, —$C(O)OR_{15}$, halo and —$C(O)NR_{13}R_{14}$.

3. The compound of claim 1 which is:

2-methyl-6-[2-oxo-1,2-dihydro-indol-(3Z)-ylidene]1,4,5,6-tetrahydro-cyclopenta[b]pyrrole-3-carboxylic acid ethyl ester;

6-[5-(2,6-dichloro-phenylmethanesulfonyl)-2-oxo-1,2-dihydro-indol-(3Z)-ylidene]-2-methyl-1,4,5,6-tetrahydro-cyclopenta[b]pyrrole-3-carboxylic acid ethyl ester;

2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid ethyl ester;

3-[2-methyl-4,5-dihydro-1H-cyclopenta[b]pyrrol(6Z)-ylidene]-2-oxo-2,3-dihydro-1H-indole-5-sulfonic acid methylamide;

2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid;

6-[5-methanesulfonyl-2-oxo-1,2-dihydro-indol-(3Z)-ylidene]-2-methyl-1,4,5,6-tetrahydro-cyclopenta[b]pyrrole-3-carboxylic acid ethyl ester;

6-[5-dimethylsulfamoyl-2-oxo-1,2-dihydro-indol(3Z)-ylidene]-2-methyl-1,4,5,6-tetrahydro-cyclopenta[b]pyrrole-3-carboxylic acid ethyl ester;

6-[5-isopropylsulfamoyl-2-oxo-1,2-dihydro-indol-(3Z)-ylidene]-2-methyl-1,4,5,6-tetrahydro-cyclopenta[b]pyrrole-3-carboxylic acid ethyl ester;

6-[5-ethanesulfonyl-2-oxo-1,2-dihydro-indol-(3Z)-ylidene]-2-methyl-1,4,5,6-tetrahydro-cyclopenta[b]pyrrole-3-carboxylic acid ethyl ester;

2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid (2-hydroxy-3-pyrrolidin-1-yl-propyl)-amide;

2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid (3-cyclopropylamino-2-hydroxy-propyl)-amide;

2-methyl-6-[5-methylsulfamoyl-2-oxo-1,2-dihydro-indol-(3Z)-ylidene]-1,4,5,6-tetrahydro-cyclopenta[b]pyrrole-3-carboxylic acid (2-dimethylamino-ethyl)-amide;

3-[2-methyl-3-((R)-2-pyrrolidin-1-ylmethyl-pyrrolidine-1-carbonyl)-4,5-dihydro-1H-cyclopenta[b]pyrrol-(6Z)-ylidene]-2-oxo-2,3-dihydro-1H-indole-5-sulfonic acid methylamide;

2-methyl-6-[2-oxo-5-sulfamoyl-1,2-dihydro-indol-(3Z)-ylidene]-1,4,5,6-tetrahydro-cyclopenta[b]pyrrole-3-carboxylic acid ethyl ester;

3-[3-methanesulfonyl-2-methyl-4,5-dihydro-1H-cyclopenta[b]pyrrol-(6Z)-ylidene]-2-oxo-2,3-dihydro-1H-indole-5-sulfonic acid methylamide;

5-fluoro-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one;

6-methoxy-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one;

4-methoxy-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one;

7-chloro-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one;

6-(4-methoxy-phenyl)-3-[2-methyl-3-((S)-2-pyrrolidin-1-ylmethyl-pyrrolidine-1-carbonyl)-4,5-dihydro-1H-cyclopenta[b]pyrrol-(6Z)-ylidene]-1,3-dihydro-indol-2-one;

or a prodrug or pharmaceutically acceptable salt thereof.

4. A pharmaceutical composition, comprising a compound, prodrug or pharmaceutically acceptable salt of claim 1 and a pharmaceutically acceptable carrier or excipient.

* * * * *